US007722868B2

(12) United States Patent
Freeman et al.

(10) Patent No.: US 7,722,868 B2
(45) Date of Patent: May 25, 2010

(54) AGENTS THAT MODULATE THE INTERACTION OF B7-1 POLYPEPTIDE WITH PD-L1 AND METHODS OF USE THEREOF

(75) Inventors: Gordon J. Freeman, Brookline, MA (US); Arlene H. Sharpe, Brookline, MA (US); Janet Buhlman, Allston, MA (US); Didier Mandelbrot, Newton, MA (US)

(73) Assignees: Dana-Farber Cancer Institute, Inc., Boston, MA (US); Brigham and Women's Hospital, Boston, MA (US)

( * ) Notice: Subject to any disclaimer, the term of this patent is extended or adjusted under 35 U.S.C. 154(b) by 0 days.

(21) Appl. No.: 11/501,392

(22) Filed: Aug. 9, 2006

(65) Prior Publication Data
US 2007/0065427 A1    Mar. 22, 2007

Related U.S. Application Data

(63) Continuation of application No. 10/293,809, filed on Nov. 12, 2002, now abandoned.

(60) Provisional application No. 60/337,817, filed on Nov. 13, 2001.

(51) Int. Cl.
*A61K 39/395* (2006.01)
(52) U.S. Cl. .................................................. 424/130.1
(58) Field of Classification Search ........................ None
See application file for complete search history.

(56) References Cited

U.S. PATENT DOCUMENTS

| | | | |
|---|---|---|---|
| 5,698,520 | A | 12/1997 | Honjo et al. |
| 5,869,050 | A | 2/1999 | de Boer et al. |
| 7,101,550 | B2 * | 9/2006 | Wood et al. ............... 424/144.1 |
| 2002/0110836 | A1 | 8/2002 | Freeman et al. |
| 2002/0164600 | A1 | 11/2002 | Freeman et al. |
| 2003/0039653 | A1 | 2/2003 | Chen et al. |

FOREIGN PATENT DOCUMENTS

| | | |
|---|---|---|
| WO | WO-WO 98/38216 | 9/1998 |
| WO | WO-01/14557 | 3/2001 |
| WO | WO-01/39722 | 6/2001 |
| WO | WO-02/078731 | 10/2002 |
| WO | WO-02/079474 | 10/2002 |

OTHER PUBLICATIONS

Agata et al., "Expression of the PD-1 antigen on the surface of stimulated mouse T and B lymphocytes," Int. Immunol., 8(5):765-772 (1996).
Aicher et al., "Characterization of human inductile costimulator ligand expression and function," J. Immunol., 164:4689-4696 (2000).
Baskar et al., "Constitutive expression of B7 restores immunogenicity of tumor cells expressing truncated major histocompatibility complex class II molecules," Proc. Natl. Acad. Sci., 90:5687-5690 (1993).
Boussiotis et al., "B7 but not intercellular adhesion molecule-1 costimulation prevents the induction of human alloantigen-specific tolerance," J. Exp. Med., 178:1753-1763(1993).
Brodie et al., "LICOS, a primordial constimulatory ligand?" Curr. Biol., 10:333-336 (2000).
Chen et al., "Costimulation of antitumor immunity by the B7 counter-receptor for the T lymphocyte molecules CD28 and CTLA-4," Cell, 71:1093-1102 (1992).
Fallarino et al., "B7-1 engagement of cytotoxic T lymphocyte antigen 4 inhibits T cell activation in the absence of CD28," J. Exp. Med., 188:205-210 (1998).
Freeman et al., "Engagement of the PD-1 inmunoinhibitory receptor by a novel B7 family member leads to negative regulation of lymphocyte activation," J. Exp. Med., 192:1027-1034 (2000).
Gimmi et al., "Human T-cell clonal anergy is induced by antigen presentation in the absence of B7 costimulation," Proc. Natl. Acad. Sci. USA, 90:6586-6590 (1993).
Greenwald et al., "The B7 Family Revisited," Annu. rev. Immunol., 23:515-548 (2005).
Harding et al., "CD28-mediated signalling co-stimulates murine T cells and prevents induction of anergy in T-cell clones," Nature, 356:607-609 (1992).
Henry et al., "Structure and evolution of the extended 87 family," Immunol. Today, 20(6):285-288 (1999).
Hutloff et al., "ICOS is an inducible T-cell co-stimulator structurally and functionally related to CD28," Nature, 397:263-266 (1999).
Ishida et al., "Induced expression of PD-1, a novel member of the immunoglobulin gene superfamily, upon programmed cell death," EMBO J., 11:3887-3895 (1992).
Krummel et al., "CTLA-4 engagement inhibits IL-2 accumulation and cell cycle progression upon activation of resting T cells," J. Exp. Med., 183:2533-2540 (1996).
Latchman et al., "PD-L2 is a second ligand for PD-1 and inhibits T cell activation," Nat. Immunol., 2:261-268 (2001).
Lenschow et al., "Long-term survival of xenogeneic pancreatic islet grafts induced by CTLA4Ig," Science, 257:789-792 (1992).
Ling et al., "Cutting edge: identification of GL50, a novel B7-like protein that functionally binds to ICOS receptor," J. Immunol., 164:1653-1657 (2000).

(Continued)

*Primary Examiner*—Ilia Ouspenski
(74) *Attorney, Agent, or Firm*—Foley Hoag, LLP

(57) ABSTRACT

Disclosed are methods for modulating an immune response including a method for inhibiting the interaction between a B7 polypeptide and a PD-1 ligand, the method comprising contacting an immune cell bearing a PD-1 ligand, or an immune cell bearing a B7 polypeptide, with an agent that inhibits the interaction between the PD-1 ligand and the B7 polypeptide. Such agents may be an anti-PD-1 ligand antibody or a small molecule. Also disclosed is a method for modulating an immune response comprising contacting an immune cell bearing the PD-1 ligand, or an immune cell bearing the PD-1 polypeptide, with an agent that inhibits interactions between the PD-1 ligand and the PD-1 polypeptide, without inhibiting interactions between the PD-1 ligand and a B7 polypeptide, to thereby modulate an immune response. The agent may be an anti-PD-1 ligand antibody or a small molecule.

7 Claims, 6 Drawing Sheets

OTHER PUBLICATIONS

Mages et al., "Molecular cloning and characterization of murine ICOS and identification of B7h as ICOS ligand," Eur. J. Immunol., 30:1040-1047(2000).

Nishimura et al., "Developmentally regulated expression of the PD-1 protein on the surface of double-negative (CD4'CD8')thymocytes," Int. Immunol., 8:773-780 (1996).

Riley et al., "The CD28 famiy: a T-cell rheostat for therapeutic control of T-cell activation," Blood, 105(1):13-21 (2005).

Shinohara et al., "Structure and chromosomal localization of the human PD-1 gene (PDCD1)." Genomics, 23:704-706(1994).

Swallow et al., B7h, a novel costimulatory homolog of B7.1 and B7.2, is induced by TNFα, Immunity, 11:423-432 (1999).

Tivol et al., "Loss of CTLA-4 leads to massive lymphoproliferation and fatal multiorgan tissue destruction, revealing a critical negative regulatory role of CTLA-4," Immunity, 3:541-547 (1995).

Townsend et al., "Tumor rejection after direct costimulation of CD8+ T cells by B7-transfected melanoma cells," Science, 259:368-370 (1993).

Turka et al, T-cell activation by the CD28 ligand B7 is required for cardiac allograft rejection in vivo, Proc. Natl. Acad. Sci. USA, 89:11102-11105 (1992).

Vivier et al., "Immunoreceptor tyrosine-based inhibition motifs," Immunol. Today, 18:286-291 (1997).

Waterhouse et al., "Lymphoproliferative disorders with early lethality in mice deficient in Ctla-4," Science, 270:985-988 (1995).

Yoshinaga et al., "T-cell co-stimulation through B7RP-1 and ICOS," Nature, 402:827-832 (1999).

Bugeon et al., "Costimulation of T cells," Am. J. Respir. Crit. Care Med., 162:S164-S168 (2000).

Butte et al., "Interaction of human PD-L1 and B7-1," Mol. Immunol., 45(13):3567-3572 (2008).

Butte et al., "Programmed Death-1 Ligand 1 Interacts Specifically with the B7-1 Costimulatory Molecule to Inhibit T Cell Responses," Immunity, 27(1):111-122 (2007).

Dong et al., "B7-H1 a third member of the B7 family, co-stimulates T cell proliferation and interleukin-10 secretion," Nature Medicine, 5(12):1365-1369 (1999).

Tseng et al., "B7-DC, a new dendritic cell molecule with potent costimulatory properties for T cells," J. Exp. Med., 193(7):839-845 (2001).

* cited by examiner

AGENTS THAT MODULATE THE INTERACTION OF B7-1 POLYPEPTIDE WITH PD-L1 AND METHODS OF USE THEREOF

RELATED APPLICATIONS

This application is a continuation of U.S. patent application Ser. No. 10/293,809, filed Nov. 12, 2002, which claims priority to U.S. Provisional Application 60/337,817, filed Nov. 13, 2001; the contents of each application are incorporated herein by reference.

GOVERNMENT FUNDING

Work described herein was supported under AI39671, CA 84500 and AI 41584, awarded by the National Institutes of Health. The U.S. government, therefore, may have certain rights in this invention.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165:302-319; Mueller, D. L. et al. (1990) *J. Immunol.* 144:3701-3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) *Annu. Rev. Immunol.* 14:233). Costimulation is neither antigen-specific, nor MHC restricted and is thought to be provided by one or more distinct cell surface polypeptides expressed by APCs (Jenkins, M. K. et al. (1988) *J. Immunol.* 140:3324-3330; Linsley, P. S. et al. (1991) *J. Exp. Med.* 173:721-730; Gimmi, C. D., et al. 1991 *Proc. Natl. Acad. Sci. USA* 88:6575-6579; Young, J. W. et al. (1992) *J. Clin. Invest.* 90:229-237; Koulova, L. et al. (1991) *J. Exp. Med.* 173:759-762; Reiser, H. et al. (1992) *Proc. Natl. Acad. Sci. USA* 89:271-275; van-Seventer, G. A. et al. (1990) *J. Immunol.* 144:4579-4586; LaSalle, J. M. et al. (1991) *J. Immunol.* 147:774-80; Dustin, M. I. et al. (1989) *J. Exp. Med.* 169:503; Armitage, R. J. et al. (1992) *Nature* 357:80-82; Liu, Y. et al. (1992) *J. Exp. Med.* 175:437-445).

The CD80 (B7-1) and CD86 (B7-2) proteins, expressed on APCs, are critical costimulatory polypeptides (Freeman et al. (1991) *J. Exp. Med.* 174:625; Freeman et al. (1989) *J. Immunol.* 143:2714; Azuma et al. (1993) *Nature* 366:76; Freeman et al. (1993) *Science* 262:909). B7-2 appears to play a predominant role during primary immune responses, while B7-1, which is upregulated later in the course of an immune response, may be important in prolonging primary T cell responses or costimulating secondary T cell responses (Bluestone (1995) *Immunity* 2:555).

One receptor to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S. et al. (1991) *J. Exp. Med.* 173:721-730; Gimmi, C. D. et al. (1991) *Proc. Natl. Acad. Sci. USA* 88:6575-6579; June, C. H. et al. (1990) *Immunol. Today.* 11:211-6; Harding, F. A. et al. (1992) *Nature* 356:607-609). A second receptor, termed CTLA4 (CD152) is homologous to CD28 but is not expressed on resting T cells and appears following T cell activation (Brunet, J. F. et al. (1987) *Nature* 328:267-270). CTLA4 appears to be critical in negative regulation of T cell responses (Waterhouse et al. (1995) *Science* 270:985). Blockade of CTLA4 has been found to remove inhibitory signals, while aggregation of CTLA4 has been found to provide inhibitory signals that downregulate T cell responses (Allison and Krummel (1995) *Science* 270:932). The B7 polypeptides have a higher affinity for CTLA4 than for CD28 (Linsley, P. S. et al. (1991) *J. Exp. Med.* 174:561-569) and B7-1 and B7-2 have been found to bind to distinct regions of the CTLA4 polypeptide and have different kinetics of binding to CTLA4 (Linsley et al. (1994) *Immunity* 1:793). A new polypeptide related to CD28 and CTLA4, ICOS, has been identified and seems to be important in IL-10 production (Hutloff et al. (1999) *Nature* 397:263; WO 98/38216), as has its ligand, which is a new B7 family member (Aicher A. et al. (2000) *J. Immunol.* 164:4689-96; Mages H. W. et al. (2000) *Eur. J. Immunol.* 30:1040-7; Brodie D. et al. (2000) *Curr. Biol.* 10:333-6; Ling V. et al. (2000) *J. Immunol.* 164:1653-7; Yoshinaga S. K. et al. (1999) *Nature* 402:827-32). If T cells are only stimulated through the T cell receptor, without receiving an additional costimulatory signal, they become nonresponsive, anergic, or die, resulting in downmodulation of the immune response.

The importance of the B7:CD28/CTLA4 costimulatory pathway has been demonstrated in vitro and in several in vivo model systems. Blockade of this costimulatory pathway results in the development of antigen specific tolerance in murine and human systems (Harding, F. A. et al. (1992) *Nature* 356:607-609; Lenschow, D. J. et al. (1992) *Science* 257:789-792; Turka, L. A. et al. (1992) *Proc. Natl. Acad. Sci. USA* 89:11102-11105; Gimmi, C. D. et al. (1993) *Proc. Natl. Acad. Sci. USA* 90:6586-6590; Boussiotis, V. et al. (1993) *J. Exp. Med.* 178:1753-1763). Conversely, expression of B7 by B7 negative murine tumor cells induces T-cell mediated specific immunity accompanied by tumor rejection and long lasting protection to tumor challenge (Chen, L. et al. (1992) *Cell* 71:1093-1102; Townsend, S. E. and Allison, J. P. (1993) *Science* 259:368-370; Baskar, S. et al. (1993) *Proc. Natl. Acad. Sci.* 90:5687-5690.).

Inhibitory receptors that bind to costimulatory polypeptides have also been identified on immune cells. Activation of CTLA4, for example, transmits a negative signal to a T cell. Engagement of CTLA4 inhibits IL-2 production and can induce cell cycle arrest (Krummel and Allison (1996) *J. Exp. Med.* 183:2533). In addition, mice that lack CTLA4 develop lymphoproliferative disease (Tivol et al. (1995) *Immunity* 3:541; Waterhouse et al. (1995) *Science* 270:985). The blockade of CTLA4 with antibodies may remove an inhibitory signal, whereas aggregation of CTLA4 with antibody transmits an inhibitory signal. Therefore, depending upon the receptor to which a costimulatory polypeptide binds (i.e., a costimulatory receptor such as CD28 or an inhibitory receptor such as CTLA4), certain B7 polypeptides can promote T cell costimulation or inhibition.

PD-1 has been identified as a receptor which binds to PD-L1 and PD-L2. PD-1 is a member of the immunoglobulin gene superfamily. PD-1 (Ishida et al. (1992) *EMBO J.* 11:3887; Shinohara et al. (1994) *Genomics* 23:704; U.S. Pat. No. 5,698,520) has an extracellular region containing immunoglobulin superfamily domain, a transmembrane domain, and an intracellular region including an immunoreceptor tyrosine-based inhibitory motif (ITIM). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 bind to B7-1 and B7-2. It has been proposed that there is a phylogenetic relationship between the MHC and B7 genes (Henry et al. (1999) *Immunol. Today* 20(6):285-8).

The nucleotide and amino acid sequence of PD-1 is published in Ishida et al. (1992) *EMBO J.* 11:3887; Shinohara et al. (1994) *Genomics* 23:704; and U.S. Pat. No. 5,698,520. PD-1 was previously identified using a subtraction cloning based approach to select for proteins involved in apoptotic cell death. PD-1 is identified herein as a member of the CD28/CTLA-4 family of polypeptides. Like CTLA4, PD-1 is rapidly induced on the surface of T-cells in response to anti-CD3 (Agata et al. (1996) *Int. Immunol.* 8:765). In contrast to CTLA4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

Two types of human PD-1 ligand polypeptides have been identified. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver while only PD-L1 is expressed in fetal liver. Both PD-1 ligands are upregulated on activated monocytes and dendritic cells.

The fact that PD-1 binds to PD-L1 and PD-L2 places PD-1 in a family of inhibitory receptors with CTLA4. While engagement of a costimulatory receptor results in a costimulatory signal in an immune cell, engagement of an inhibitory receptor, e.g., CTLA4 or PD-1 (for example by crosslinking or by aggregation), leads to the transmission of an inhibitory signal in an immune cell, resulting in downmodulation of immune cell responses and/or in immune cell energy. While transmission of an inhibitory signal leads to downmodulation in immune cell responses (and a resulting downmodulation in the overall immune response), the prevention of an inhibitory signal (e.g., by using a non-activating antibody against PD-1) in immune cells leads to upmodulation of immune cell responses (and a resulting upmodulation of an immune response).

The identification of additional agents useful in modulation of an immune response would be of tremendous benefit.

SUMMARY OF THE INVENTION

The present invention is based, at least in part, on the discovery that PD-1 ligand, in addition to binding PD-1, binds to B7-1. PD-1 transmits a negative signal to immune cells, similar to CTLA4. PD-1 ligand polypeptides are expressed on the surface of antigen presenting cells and can provide a costimulatory signal to immune cells or can transmit downmodulatory signals to immune cells, depending upon the polypeptide to which they bind. For example, PD-1 ligand binding to PD-1 transmits a negative signal, whereas PD-1 ligand binding to a B7 polypeptide does not. Thus, modulation of the interaction between PD-1 and PD-1 ligand or between PD-1 ligand and a B7 polypeptide results in modulation of the immune response.

Thus, one aspect of the invention relates to a method for inhibiting the interaction between a B7 polypeptide and a PD-1 ligand. The method comprises contacting an immune cell bearing a PD-1 ligand, or an immune cell bearing a B7 polypeptide, with an agent that inhibits the interaction between the PD-1 ligand and the B7 polypeptide. In one embodiment, the interaction between a B7 polypeptide and a PD-1 ligand polypeptide prevents PD-1 ligand from binding to PD-1 and, thus, inhibits delivery of an inhibitory immune signal. In one embodiment, agents which block the interaction between PD-1 and PD-1 ligand can prevent inhibitory signaling. In one embodiment, agents that block the binding of a B7 polypeptide to a PD-1 ligand allow the PD-1 ligand to bind PD-1, and provide an inhibitory signal to an immune cell, thus enhancing signaling inhibition.

PD-L1, by binding to a B7 polypeptide, also reduces the B7 polypeptide binding to the inhibitory receptor CTLA4. In one embodiment, agents that block the binding of a B7 polypeptide to a PD-1 ligand polypeptide allow the B7 polypeptide to bind CTLA4 and provide an inhibitory signal to an immune cell, and agents that promote the binding of the B7 polypeptide to the PD-1 ligand inhibit binding of the B7 polypeptide to CTLA4, and thus inhibit a negative signal.

In another embodiment, a PD-1 ligand, by binding to a B7 polypeptide, also reduces the B7 polypeptide binding to the costimulatory receptor CD28. Thus, in one embodiment, agents that block the binding of a the B7 polypeptide to the PD-1 ligand polypeptide allow the B7 polypeptide to bind CD28 and provide a costimulatory signal to an immune cell and agents that promote the binding of the B7 polypeptide to the PD-1 ligand inhibit the binding of the B7 polypeptide to CD28, and thereby inhibit a costimulatory signal.

Accordingly, one aspect of the invention relates to a method for modulating (e.g., inhibiting or stimulating) an immune response, comprising contacting an immune cell bearing a PD-1 ligand or an immune cell bearing a B7 polypeptide with an agent that modulates (e.g., inhibits or stimulates) the interaction between the PD-1 ligand and the B7 polypeptide, to thereby modulate (e.g., inhibit or stimulate) the immune response.

In one embodiment, the agent is an anti-PD-1 ligand antibody.

In one embodiment, the agent is an anti-B7-1 antibody.

In one embodiment, the agent is a small molecule.

In one embodiment, the agent is a peptide.

In one embodiment, the agent is a fusion protein.

Another aspect of the invention relates to a method for modulating an immune response comprising, contacting an immune cell bearing a PD-1 ligand, or an immune cell bearing PD-1, with an agent that inhibits the interaction between the PD-1 ligand and PD-1, without inhibiting an interaction between a PD-1 ligand and a B7 polypeptide, to thereby modulate the immune response.

In one embodiment, the agent is an anti-PD-1 ligand antibody, an anti-PD-1 antibody, a peptide, or a small molecule, wherein the agent inhibits the interaction between PD-1 and a PD-1 ligand, and does not inhibit the interaction between the PD-1 ligand and a B7 polypeptide.

In one embodiment, the PD-1 ligand is PD-L1.

In one embodiment, the PD-1 ligand is PD-L2.

In one embodiment, the B7 polypeptide is B7-1

Another aspect of the invention relates to a method for modulating an immune response by inhibiting the interaction between a B7 polypeptide on a first immune cell and CTLA4 on a second immune cell, comprising contacting said first or second immune cell with a PD-1 ligand, to thereby modulate the immune response.

Another aspect of the invention relates to a method for modulating an immune response comprising contacting an immune cell bearing a B7 polypeptide, or an immune cell bearing a CTLA4 polypeptide with an agent that inhibits the interaction between a B7 polypeptide and a CTLA4 polypeptide, and does not inhibit the interaction between a B7 polypeptide and the PD-1 ligand, to thereby modulate an immune response.

Yet another aspect of the invention relates to a method of modulating an immune response by inhibiting the interaction between a B7 polypeptide on a first immune cell and CD28 on a second immune cell, comprising contacting said first or second immune cell with a PD-1 ligand, to thereby modulate an immune response.

Another aspect of the invention relates to a method for modulating an immune response comprising contacting an immune cell bearing a B7 polypeptide, or an immune cell bearing CD28, with an agent that inhibits the interaction between the B7 polypeptide and a CD28, and does not inhibit the interaction between the B7 polypeptide and the PD-1 ligand, to thereby modulate the immune response.

Another aspect of the invention relates to a method for identifying an agent that modulates an immune response, comprising, screening for agents which inhibit the interaction between a PD-1 ligand and a PD-1 polypeptide, and determining whether the agents identified in the screen inhibit the interaction between a PD-1 ligand and a B7 polypeptide, wherein an agent identified in the screen which is determined not to affect (e.g., inhibit) the interaction between a PD-1 ligand and a B7 polypeptide, is identified as an agent that modulates the immune response.

Another aspect of the invention relates to a method for identifying an agent that modulates an immune response, comprising, screening for agents which inhibit the interaction between a B7 polypeptide and CTL4, and determining whether the agents identified in the screen inhibit the interaction between a PD-1 ligand and the B7 polypeptide, wherein an agent identified in the screen which is determined not to affect (e.g., inhibit) the interaction between the B7 polypeptide and CTLA4, but does not inhibit the interaction between the B7 polypeptide and the PD-1 ligand, is identified as an agent that modulates the immune response.

Yet another aspect of the invention relates to a method for identifying an agent that modulates an immune response comprising, screening for agents which inhibit the interaction between a PD-1 ligand and a B7 polypeptide, and determining whether the agents identified in the screen inhibit the interaction between the PD-1 ligand and the B7 polypeptide, wherein an agent identified in the screen which is determined not to affect (e.g., inhibit) the interaction between a PD-1 ligand and a PD-1 polypeptide, is identified as an agent that modulates the immune response.

DETAILED DESCRIPTION OF THE INVENTION

I. Definitions

Figure 1:
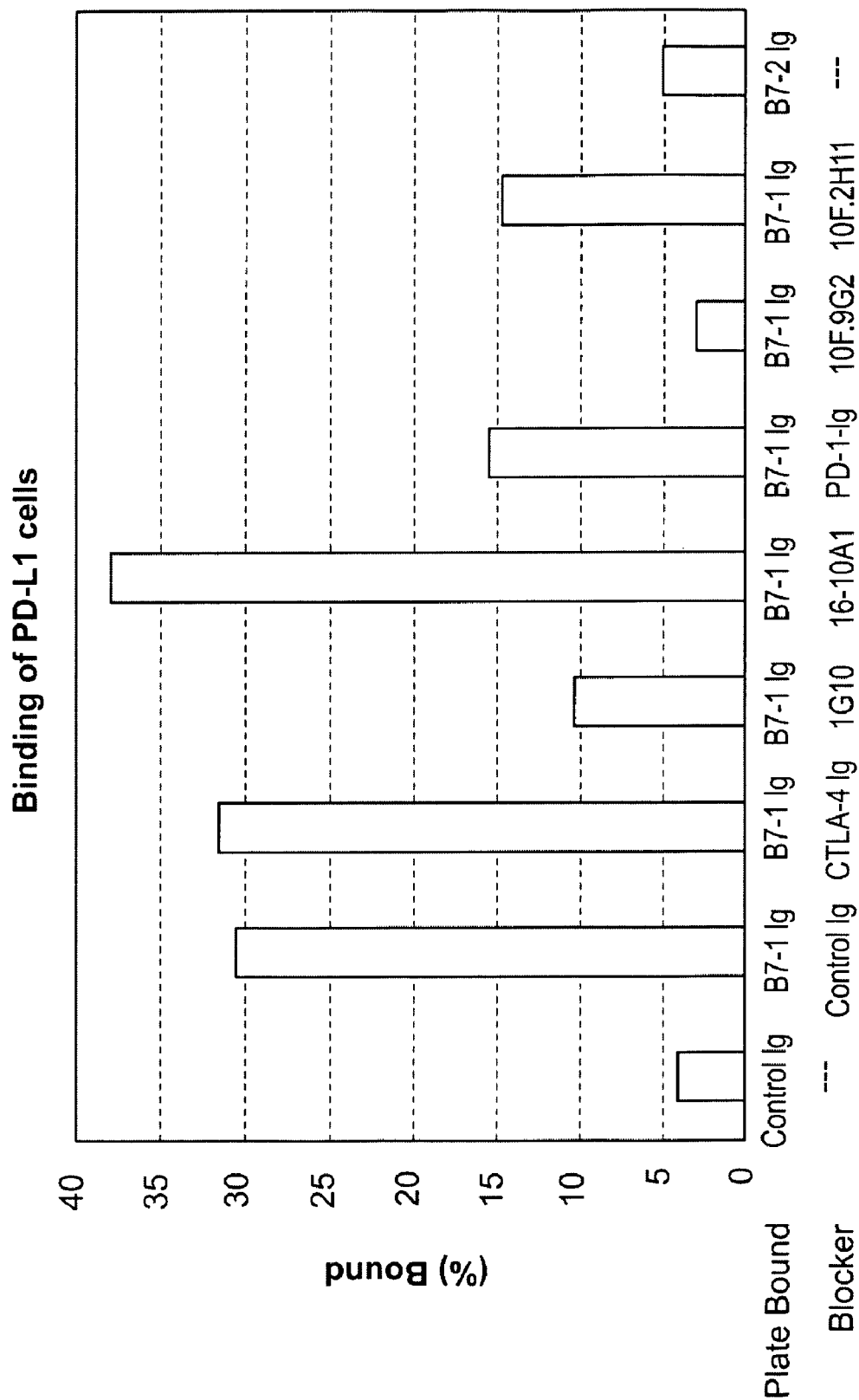
FIG. 1 is a bar graph of data representing the binding of cells expressing PD-L1 to B7-1 Ig, in the presence of absence of 1G10 (anti-B7-1) antibody, 10F.9G2 (anti-PD-1) antibody, 10F.2H11 (anti-PD-1) antibody, and PD-1 Ig polypeptide.

As used herein, the term "modulate" includes up-regulation and down-regulation, e.g., enhancing or inhibiting a response.

As used herein, the term "inhibit" includes the decrease, limitation, or blockage, of, for example a particular action, function, or interaction.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4 or PD-1). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory polypeptides (Fallarino et al. (1998) J. Exp. Med. 188:205). Transmission of an inhibitory signal to an immune cell can result in unresponsiveness or energy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

Depending upon the form of the PD-1 ligand polypeptide that binds to a receptor, a signal can either be transmitted (e.g., by a multivalent form of a PD-1 ligand polypeptide or a form of a PD-1 ligand polypeptide that binds to Fc receptors that results in crosslinking of receptor) or a signal can be inhibited (e.g., by a soluble, monovalent form of a PD-1 ligand polypeptide or a form of PD-1 ligand polypeptide lacking Fc receptors), for instance by competing with activating forms of PD-1 ligand polypeptides for binding to the receptor. However, there are instances in which a soluble polypeptide can be stimulatory. The effects of a modulatory agent can be easily demonstrated using routine screening assays as described herein.

As used herein, the term "costimulate," as used with reference to activated immune cells, includes the ability of a costimulatory polypeptide to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

As used herein, the term "activating receptor" includes immune cell receptors that bind antigen, complexed antigen (e.g., in the context of MHC polypeptides), or bind to antibodies. Such activating receptors include T cell receptors (TCR), B cell receptors (BCR), cytokine receptors, LPS receptors, complement receptors, and Fc receptors.

T cell receptors are present on T cells and are associated with CD3 polypeptides. T cell receptors are stimulated by antigen in the context of MHC polypeptides (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

B cell receptors are present on B cells. B cell antigen receptors are a complex between membrane Ig (mIg) and other transmembrane polypeptides (e.g., Igα and Igβ). The signal transduction function of mIg is triggered by crosslinking of receptor polypeptides by oligomeric or multimeric antigens. B cells can also be activated by anti-immunoglobulin antibodies. Upon BCR activation, numerous changes occur in B cells, including tyrosine phosphorylation.

Fc receptors are found on many cells which participate in immune responses. Fc receptors (FcRs) are cell surface receptors for the Fc portion of immunoglobulin polypeptides (Igs). Among the human FcRs that have been identified so far are those which recognize IgG (designated Fcγ R), IgE (Fcε R1), IgA (Fcα), and polymerized IgM/A (Fcμα R). FcRs are found in the following cell types: Fcε R I (mast cells), Fcε R.II (many leukocytes), Fcα R (neutrophils), and Fcμα R (glandular epithelium, hepatocytes) (Hogg, N. (1988) *Immunol. Today* 9:185-86). The widely studied FcγRs are central in cellular immune defenses, and are responsible for stimulating the release of mediators of inflammation and hydrolytic enzymes involved in the pathogenesis of autoimmune disease (Unkeless, J. C. et al. (1988) *Annu. Rev. Immunol.* 6:251-81). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/macrophages), hFcγ RII (on monocytes, neutrophils, eosinophils, platelets, possibly B cells, and the K562 cell line), and Fcγ III (on NK cells, neutrophils, eosinophils, and macrophages).

With respect to T cells, transmission of a costimulatory signal to a T cell involves a signaling pathway that is not inhibited by cyclosporine A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

As used herein, the term "inhibitory signal" refers to a signal transmitted via an inhibitory receptor (e.g., CTLA4 or PD-1) for a polypeptide on a immune cell. Such a signal antagonizes a signal via an activating receptor (e.g., via a TCR, CD3, BCR, or Fc polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

The PD-1 ligands and B7 polypeptides comprise a family of polypeptides having certain conserved structural and functional features. Similarly, the PD-1 proteins are members of a family of polypeptides having conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. The PD-1 ligand polypeptides described herein are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

As used herein, the term "activity," when used with respect to a polypeptide, e.g., a PD-1 ligand, PD-1, CTLA4, CD28, or a B7 polypeptide includes activities which are inherent in the structure of the protein. For example, with regard to PD-1 ligand, the term "activity" includes the ability to modulate immune cell costimulation (e.g. by modulating a costimulatory signal in an activated immune cell) or to modulate inhibition by modulating an inhibitory signal in an immune cell (e.g., by engaging a natural receptor on an immune cell) Those of skill in the art will recognize that when an activating form of the PD-1 ligand polypeptide binds to a costimulatory receptor, a costimulatory signal is generated in the immune cell. When an activating form of the PD-1 ligand polypeptide binds to an inhibitory receptor, an inhibitory signal is generated in the immune cell. When a PD-1 ligand binds to a B7 polypeptide, a costimulatory signal may be generated because the inhibitory signal of the PD-1 ligand binding to PD-1 is inhibited.

As used herein, the term "PD-1 ligand" includes both PD-L1 (Freeman et al. (2000) *J. Exp. Med.* 192:1027) and PD-L2 (Latchman et al. (2001) *Nat. Immunol.* 2:261).

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

With respect to PD-1, the term "activity" includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

As used herein, a "naturally-occurring" nucleic acid polypeptide refers to an RNA or DNA polypeptide having a nucleotide sequence that occurs in nature (e.g., encodes a natural protein).

As used herein, an "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of PD-1 ligand, PD-1 or B7 polypeptide, in which the protein is separated from cellular components of the cells from which it is isolated or recombinantly produced. In one embodiment, the language "substantially free of cellular material" includes preparations of PD-1 ligand, PD-1 or B7 fusion protein, having less than about 30% (by dry weight) of non-PD-1 ligand, PD-1 or B7 fusion protein (also referred to herein as a "contaminating protein"), more preferably less than about 20% of non-PD-1 ligand, PD-1 or B7 fusion protein, still more preferably less than about 10% of PD-1 ligand, PD-1 or B7 fusion protein, and most preferably less than about 5% non-PD-1 ligand, PD-1 or B7 fusion protein. When antibody, polypeptide, peptide or fusion protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., PD-1 ligand or a B7 polypeptide). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to PD-1 ligand, PD-1, or B7-1 polypeptides. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds PD-1 ligand is substantially free of antibodies that specifically bind antigens other than PD-1 ligand). Moreover, an isolated antibody may be substantially free of other cellular material and/or chemicals.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

II. Agents that Modulate Immune Cell Activation

The agents of this invention can up or down regulate the immune system and, thereby, up or downregulate an immune response. For example, modulation of the interaction between PD-1 and PD-1 ligand, or between PD-1 ligand and a B7 polypeptide, results in modulation of the immune response. The interaction between a B7 polypeptide and a PD-1 ligand polypeptide prevents PD-1 ligand from binding to PD-1 and, thus, inhibits delivery of an inhibitory immune signal. Thus, in one embodiment, agents which block the interaction between PD-1 and PD-1 ligand can prevent inhibitory signaling. In one embodiment, agents that block the binding of a B7 polypeptide to a PD-1 ligand polypeptide allow PD-1 ligand to bind PD-1 and provide an inhibitory signal to an immune cell. PD-1 ligand, by binding to a B7 polypeptide, also reduces the B7 polypeptide binding to the inhibitory receptor CTLA4. In one embodiment, agents that block the binding of a B7 polypeptide to a PD-1 ligand polypeptide allow the B7 polypeptide to bind CTLA4 and provide an inhibitory signal to an immune cell. In another embodiment, PD-L1, by binding to a B7 polypeptide, also reduces the B7 polypeptide binding to the costimulatory receptor CD28. Thus, in one embodiment, agents that block the binding of a B7 polypeptide to a PD-1 ligand polypeptide allow the B7 polypeptide to bind CD28, and provide a costimulatory signal to an immune cell.

For example, in one embodiment, agents that increase the interaction between a PD-1 ligand and a B7 polypeptide can enhance an immune response while agents that decrease the interaction between a PD-1 ligand and a B7 polypeptide can reduce an immune response by enhancing the interaction between the PD-1 ligand and PD-1 and/or the interaction between the B7 polypeptide and CTLA4. In one embodiment, agents that modulate the interaction between a PD-1 ligand and a B7 polypeptide do not produce inhibition of the interaction between a PD-1 ligand and PD-1 and/or between the B7 polypeptide and CTLA4. In another embodiment, agents that increase a PD-1 ligand interaction with a B7 polypeptide, also decrease the interaction between the PD-1 ligand and PD-1, and/or between the B7 polypeptide and CTLA4. In yet another embodiment, agents that decrease the interaction of a PD-1 ligand and a B7 polypeptide, enhance or increase the interaction between the PD-1 ligand and PD-1, and/or between the B7 polypeptide and CTLA4. Exemplary agents for modulating (e.g., reducing, an immune response) include antibodies against a PD-1 ligand or a B7 polypeptide which inhibit the interaction of the PD-1 ligand with the B7 polypeptide; small molecules or peptides which inhibit the interaction of the PD-1 ligand with the B7 polypeptide; and fusion proteins (e.g. the extracellular portion of the PD-1 ligand or B7 polypeptide, fused to the Fc portion of an antibody) which bind to the B7 polypeptide or PD-1 ligand, respectively, and prevent the interaction between the PD-1 ligand and B7 polypeptide.

In another embodiment, agents that increase the interaction between a PD-1 ligand and a B7 polypeptide, decrease an immune response by decreasing the ability of the B7 polypeptide to bind to CD28. In yet another embodiment, agents that decrease the interaction between a PD-1 ligand and a B7 polypeptide can increase the immune response by increasing the interaction between the B7 polypeptide and CD28.

Agents that modulate the interaction between a PD-1 ligand and a PD-1 polypeptide can also be used to up or down regulate the immune response. For example, agents that increase the interaction between the PD-1 ligand and PD-1 polypeptide can decrease an immune response while agents that decrease the interaction between the PD-1 ligand and PD-1 polypeptide can increase an immune response. Preferably, agents that modulate the interaction between the PD-1 ligand and PD-1, do not modulate (have no direct affect on) the interaction between the PD-1 ligand and a B7 polypeptide. In another embodiment, agents that increase the interaction between the PD-1 ligand and PD-1, decrease the interaction between the PD-1 ligand and the B7 polypeptide. In yet another embodiment, agents that decrease the interaction between the PD-L1 ligand and PD-1 increase the interaction between the PD-1 ligand and the B7 polypeptide. Exemplary agents for modulating (e.g., enhancing, an immune response) include antibodies against PD-1 or a PD-1 ligand which block the interaction between PD-1 and the PD-1 ligand; small molecules or peptides which block the interaction between PD-1 and the PD-1 ligand; and fusion proteins (e.g. the extracellular portion of a PD-1 ligand or PD-1 polypeptide fused to the Fc portion of an antibody) which bind to PD-1 or a PD-1 ligand and prevent the interaction between the PD-1 ligand and PD-1.

In another embodiment, at least a portion of a PD-1 ligand which binds to a B7 polypeptide, or a mimetic of such a portion, can be used to enhance an immune response by binding to the B7 polypeptide and inhibiting the interaction between the B7 polypeptide on a first immune cell and CTLA4 on a second immune cell.

In another embodiment, at least a portion of a PD-1 ligand which binds to a B7 polypeptide, or a mimetic of such a portion, can be used to inhibit an immune response by binding to the B7 polypeptide and inhibiting the interaction between the B7 polypeptide on a first immune cell and CD28 on a second immune cell.

An isolated PD-1, PD-1 ligand, B7 polypeptide, CTLA4, or CD28, or a portion or fragment thereof (or a nucleic acid encoding such a polypeptide), can be used as an immunogen to generate antibodies that bind to the respective PD-1, PD-1 ligand, B7 polypeptide, CTLA4, or CD28, using standard techniques for polyclonal and monoclonal antibody preparation. A full-length PD-1, PD-1 ligand, B7 polypeptide, CTLA4, or CD28 can be used, or alternatively, the invention relates to antigenic peptide fragments of PD-1, PD-1 ligand, B7, CTLA4, or a CD28 polypeptide for use as immunogens. An antigenic peptide of PD-1, PD-1 ligand, B7 polypeptide, CTLA4, or CD28 comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptides are regions of PD-1, PD-1 ligand, a B7 polypeptide, CTLA4, or CD28 that are located on the surface of the protein, e.g., hydrophilic regions. A standard hydrophobicity analysis of the polypeptide molecule can be performed to identify hydrophilic regions. Highly preferred epitopes encompassed by the antigenic peptides are the regions of the polypeptide molecule which are in the extracellular domain, and therefore are involved in binding. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody binds substantially specifically to PD-1 without binding to a B7 polypeptide or a PD-1 ligand. In another embodiment, an antibody binds substantially specifically to a PD-1 ligand. In another embodiment, an antibody binds substantially specifically to a B7 polypeptide. In a preferred embodiment, an antibody binds to a PD-1 ligand and blocks the interaction between the PD-1 ligand and a B7 polypeptide. In another preferred embodiment, an antibody binds to a B7 polypeptide and blocks the interaction between a PD-1 ligand and the B7 polypeptide. In another preferred embodiment, an antibody binds to a PD-1 ligand and blocks the interaction between PD-1 and the PD-1 ligand, without blocking the interaction between the PD-1 ligand and a B7 polypeptide.

A PD-1, PD-1 ligand, B7 polypeptide, CTLA4, or CD28 immunogen typically is used to prepare antibodies by immunizing a suitable subject, (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-PD-1, anti-PD-1 ligand or anti-B7 polypeptide monoclonal antibody (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides antibody can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-PD-1, anti-PD-1 ligand or anti-B7 polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology (NY)* 12:396-399; Chen, S-Y. et al. (1994) *Hum. Gene Ther.* 5:595-601; Duan, L et al. (1994) *Proc. Natl. Acad. Sci.*

USA 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

Additionally, fully human antibodies could be made against a PD-1 ligand, PD-1, or a B7 polypeptide. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified PD-1 ligand, PD-1, or a B7 polypeptide. Spleen cells are harvested and fused to myeloma cells to produce hybridomas. Hybridomas are selected based on their ability to produce antibodies which bind to PD-1 ligand, PD-1 or a B7 polypeptide. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to PD-1, PD-1 ligand, B7, CTLA4, or a CD28 polypeptide. In one embodiment, the bispecific antibody could specifically bind to both PD-1 ligand and a B7 polypeptide.

Yet another aspect of the invention pertains to anti-PD-1, anti-PD-1 ligand or anti-B7 polypeptide antibodies that are obtainable by a process comprising, immunizing an animal with an immunogenic PD-1, PD-1 ligand, B7 polypeptide, CTLA4, or CD28, or an immunogenic portion thereof unique to PD-1, the PD-1 ligand, the B7 polypeptide, CTLA4, or CD28; and then isolating from the animal antibodies that specifically bind to the polypeptide.

In another aspect of this invention, peptides or peptide mimetics can be used to antagonize or promote the interaction between a PD-1 ligand and a B7 polypeptide or the interaction between PD-1 and a PD-1 ligand (e.g., without interfering with the interaction between the PD-1 ligand and the B7 polypeptide). In one embodiment, variants of PD-1, a PD-1 ligand, a B7 polypeptide, CTLA4, or CD28 which function as a modulating agent for the respective full length protein, can be identified by screening combinatorial libraries of mutants, e.g., truncation mutants, for antagonist activity. In one embodiment, a variegated library of PD-1, a PD-1 ligand, a B7 polypeptide, CTLA4, or CD28 variants is generated by combinatorial mutagenesis at the nucleic acid level and is encoded by a variegated gene library. A variegated library of PD-1, a PD-1 ligand, a B7 polypeptide, CTLA4, or CD28 variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of PD-1, a PD-1 ligand, a B7 polypeptide, CTLA4, or CD28 (Arkin and Youvan (1992) *Proc. Natl. Acad. Sci. USA* 89:7811-7815; Delagrave et al. (1993) *Protein Eng.* 6(3):327-331). In one embodiment, cell based assays can be exploited to analyze a variegated polypeptide library. For example, a library of expression vectors can be transfected into a cell line which ordinarily synthesizes PD-1, a PD-1 ligand, a B7 polypeptide, CTLA4, or CD28. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences of disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

In a one embodiment, the peptide has an amino acid sequence identical or similar to the B7 binding site of a PD-1 ligand polypeptide. In another embodiment, the peptide has an amino acid sequence identical or similar to the PD-L1 binding site of a B7 polypeptide. In one embodiment, the peptide competes with PD-1 ligand for binding to a B7 polypeptide or the peptide competes with a B7 polypeptide for binding to PD-1 ligand. In a preferred embodiment, the peptide competes for the binding of PD-1 ligand to a B7 polypeptide, but not for the binding between PD-1 and PD-1 ligand. In another embodiment, the peptide competes for the binding between PD-1 and PD-1 ligand but not between PD-1 ligand and a B7 polypeptide.

Peptides can be produced, typically by direct chemical synthesis, and used e.g., as antagonists of the interaction between PD-1 and PD-1 ligand or between PD-1 ligand and a B7 polypeptide. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used, therapeutically to treat disease, e.g., by altering costimulation in a patient.

Peptidomimetics (Fauchere, J. (1986) *Adv. Drug Res.* 15:29; Veber and Freidinger, (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human PD-1, a PD-1 ligand, a B7 polypeptide, CTLA4, or CD28, but have one or more peptide linkages optionally replaced by a linkage selected from the group consisting of: —CH2NH—, —CH2S—, —CH2-CH2-, —CH=CH— (cis and trans), —COCH2-, —CH(OH)CH2-, and —CH2SO—, by methods known in the art and further described in the following references: Spatola, A. F. in *"Chemistry and Biochemistry of Amino Acids, Peptides, and Proteins"* Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans.* I. 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH)CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic. Also encompassed by the present invention are small molecules which can modulate (either enhance or inhibit) interactions, e.g., the interaction between PD-1 ligand and a B7 polypeptide or between PD-1 and PD-1 ligand. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

In one embodiment, the small molecule binds to the binding site involved in the PD-1 ligand/B7 polypeptide interaction, or to the binding site involved in the PD-1/PD-1 ligand interaction. In one embodiment, the small molecule antagonizes the interaction between PD-1 ligand and a B7 polypeptide. In a preferred embodiment, the small molecule antagonizes the interaction between PD-1 ligand and a B7 polypeptide, but not the interaction between PD-1 and PD-1 ligand or between B7 and CTLA4. In another embodiment, the small molecule antagonizes the interaction between PD-1 and PD-1 ligand or between B7 and CTLA4 without antagonizing the interaction between PD-1 ligand and a B7 polypeptide.

The invention also relates to PD-1, PD-1 ligand, B7 polypeptide, CTLA4, or CD28 chimeric or fusion proteins. As used herein, a PD-1, PD-1 ligand, B7 polypeptide, CTLA4, or CD28 "chimeric protein" or "fusion protein" comprises a PD-1, PD-1 ligand, B7 polypeptide, CTLA4, or CD28 molecule operatively linked to a non-PD-1, non-PD-1 ligand, non-CTLA4, non-CD28, or non-B7 polypeptide molecule. A "PD-1, PD-1 ligand, B7 polypeptide, CTLA4, or CD28 molecule" refers to a polypeptide having an amino acid sequence corresponding to PD-1, PD-1 ligand, B7 polypeptide, CTLA4, or CD28, whereas a "a non PD-1, non-PD-1 ligand, non-B7 polypeptide, non-CTLA4, or non-CD28, molecule" refers to a polypeptide having an amino acid sequence corresponding to a protein which is not substantially homologous to the respective PD-1, PD-1 ligand, B7 polypeptide, CTLA4, or CD28 molecule, e.g., a protein which is different from the PD-1, PD-1 ligand, B7 polypeptide, CTLA4, or CD28 molecule, and which is derived from the same or a different organism. Within a PD-1, PD-1 ligand, B7 polypeptide, CTLA4, or CD28 fusion protein, the PD-1, PD-1 ligand, B7 polypeptide, CTLA4, or CD28 portion can correspond to all or a portion of a full length PD-1, PD-1 ligand, B7 polypeptide, CTLA4, or CD28 molecule. In a preferred embodiment, the fusion protein comprises at least one biologically active portion of a PD-1, PD-1 ligand, B7 polypeptide, CTLA4, or CD28 molecule, e.g., an extracellular domain. Within the fusion protein, the term "operatively linked" is intended to indicate that the PD-1, PD-1 ligand, B7 polypeptide, CTLA4, or CD28 amino acid sequences and the non PD-1, non-PD-1 ligand or non-B7 polypeptide sequences are fused in-frame to each other in such a way as to preserve functions exhibited when expressed independently of the fusion. The non PD-1, non-PD-1 ligand, non-B7 polypeptide, non-CTLA4, or non-CD28 molecules can be fused to the N-terminus or C-terminus of the PD-1, PD-1 ligand, B7 polypeptide, CTLA4, or CD28 sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. Preferably, the first peptide consists of a portion of the PD-1, PD-1 ligand, B7 polypeptide, CTLA4, or CD28 that is sufficient to modulate costimulation or inhibition of activated immune cells. In another preferred embodiment, the first peptide consists of a portion of a biologically active molecule (e.g the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Particularly preferred Ig fusion proteins include the extracellular domain portion or variable region-like domain of human PD-1, a PD-1 ligand, a B7 polypeptide, CTLA4, or CD28, coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of PD-1, a PD-1 ligand, a B7 polypeptide, CTLA4, or CD28 can be joined to DNA encoding the hinge, CH2 and CH3 regions of human IgGγ1 and/or IgGγ4 modified by site directed mutagenesis, e.g., as taught in WO 97/28267.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in*

*Molecular Biology*, eds. Ausubel et al. John Wiley & Sons: 1992). A polypeptide encoding nucleic acid can be cloned into such an expression vector such that the fusion moiety is linked in-frame to the PD-1, PD-1 ligand, B7 polypeptide, CTLA4, or CD28 encoding sequences.

In another embodiment, the fusion protein contains a heterologous signal sequence at its N-terminus. In certain host cells (e.g., mammalian host cells), expression and/or secretion of a polypeptide can be increased through use of a heterologous signal sequence.

In a preferred embodiment, the fusion protein binds to PD-1 or PD-1 ligand and blocks the interaction of PD-1 with PD-1 ligand, without blocking the interaction between PD-1 ligand and a B7 polypeptide. In another preferred embodiment, the PD-1 ligand or B7 polypeptide fusion proteins bind to PD-1 ligand or a B7 polypeptide and block the interaction between PD-1 ligand and the B7 polypeptide.

Use of PD-1, a PD-1 ligand, a B7 polypeptide, CTLA4, or CD28 fusion proteins can be useful therapeutically for the treatment of immunological disorders, e.g., autoimmune diseases, or in the case of inhibiting rejection of transplants.

The fusion proteins of the invention can be used as immunogens to produce antibodies in a subject. Such antibodies may be used to purify the respective natural polypeptides from which the fusion proteins were generated, or in screening assays to identify polypeptides which inhibit the interaction of a PD-1 ligand with a B7 polypeptide or the interaction of PD-1 with a PD-1 ligand.

The modulatory agents described herein (e.g. antibodies, small molecules, peptides, or fusion proteins) can be incorporated into pharmaceutical compositions and administered to a subject in vivo. The compositions may contain a single such molecule or agent or any combination of modulatory agents described herein.

III. Methods of Selecting Agents that Modulate Immune Cell Activation

Another aspect of the invention relates to methods of selecting agents (e.g., antibodies, fusion proteins, peptides, or small molecules) which modulate an immune response by modulating costimulation (such as agents that inhibit the interaction of PD-1 ligand with a B7 polypeptide or the interaction of PD-1 with a PD-1 ligand). Such methods utilize screening assays, including cell based and non-cell based assays. In one embodiment, the assays provide a method for identifying agents which inhibit the interaction of a PD-1 ligand and PD-1 (e.g., with or without inhibiting the interaction of PD-1 ligand and a B7 polypeptide). In another embodiment, the assays provide a method for identifying agents which modulate the interaction between a PD-1 ligand and a B7 polypeptide (e.g., with or without inhibiting the interaction of the PD-1 ligand and PD-1; the interaction of the B7 polypeptide and CTLA4; and/or the interaction of the B7 polypeptide and CD28).

In one embodiment, the invention relates to assays for screening candidate or test compounds which bind to, or modulate the activity of, PD-1, a PD-1 ligand, a B7 polypeptide, CTLA4, or CD28, e.g., modulate the ability of a PD-1 ligand or PD-1 to interact with (e.g. bind to) its cognate binding partner. In one embodiment, a method for identifying an agent to modulate an immune response entails determining the ability of the agent to modulate, e.g. enhance or inhibit, the interaction between PD-1 and a PD-1 ligand, and further determining the ability of the agent to modulate the interaction between a PD-1 ligand and a B7 polypeptide. In one embodiment, an agent that modulates the interaction between the PD-1 ligand and PD-1 (e.g., without modulating the interaction between the PD-1 ligand and the B7 polypeptide is selected). In another embodiment, an agent that modulates the interaction between a PD-1 ligand and a B7 polypeptide (e.g., without modulating the interaction between the PD-1 ligand and PD-1) is selected. Such agents include, without limitation, antibodies, proteins, fusion proteins and small molecules.

In one embodiment, a method for identifying an agent which enhances an immune response entails determining the ability of the candidate agent to enhance the interaction between a PD-1 ligand and a B7 polypeptide (e.g., without modulating or while inhibiting the interaction between the PD-1 ligand and PD-1). In another embodiment, the method entails determining the ability of the candidate agent to inhibit the interaction between a PD-1 ligand and PD-1 (e.g., without modulating or while enhancing the interaction between the PD-1 ligand and a B7 polypeptide).

In another embodiment, a method for identifying an agent to decrease an immune response entails determining the ability of a candidate agent to inhibit the interaction between a PD-1 ligand and a B7 polypeptide (e.g., without modulating or while enhancing the interaction between the PD-1 ligand and PD-1) and selecting an agent that inhibits the interaction between the PD-1 ligand and the B7 polypeptide. In another embodiment, a method for identifying an agent to decrease an immune response entails determining the ability of the candidate agent to enhance the interaction between a PD-1 ligand and PD-1 (e.g., that does not modulate, or inhibits, the interaction between the PD-1 ligand and the B7 polypeptide) and selecting an agent that enhances the interaction between the PD-1 ligand and PD-1. In a preferred embodiment, the agent selected for decreasing an immune response inhibits the interaction between the PD-1 ligand and a B7 polypeptide, but does not inhibit the interaction between the PD-1 ligand and PD-1.

In one embodiment, an assay is a cell-based assay, comprising contacting a cell expressing PD-1, a PD-1 ligand, a B7 polypeptide, CTLA4, or CD28, with a test compound and determining the ability of the test compound to modulate (e.g. stimulate or inhibit) the binding of PD-1, the PD-1 ligand, the B7 polypeptide, CTLA4, or CD28 target to its binding partner. Determining the ability of the PD-1, PD-1 ligand or B7 polypeptide to bind to, or interact with, its binding partner can be accomplished, e.g., by measuring direct binding or by measuring a parameter of immune cell activation.

For example, in a direct binding assay, the PD-1, PD-1 ligand or B7 polypeptide protein (or their respective target polypeptides) can be coupled with a radioisotope or enzymatic label such that binding of PD-1 ligand to PD-1 or to the B7 polypeptide can be determined by detecting the labeled protein in a complex. For example, PD-1, PD-1 ligand, B7 polypeptide, CTLA4, or CD28 can be labeled with $^{125}I$, $^{35}S$, $^{14}C$, or $^{3}H$, either directly or indirectly, and the radioisotope detected by direct counting of radioemmission or by scintillation counting. Alternatively, PD-1, PD-1 ligand, B7 polypeptide, CTLA4, or CD28 can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between PD-1 and a PD-1 ligand or between a PD-1 ligand and a B7 polypeptide, without the labeling of any of the interactants. For example, a microphysiometer can be used to detect the interaction of PD-1 and a PD-1 ligand, or between a PD-1 ligand and a B7 polypeptide, with its target polypeptide, without the labeling of either PD-1, PD-1 ligand, B7 polypeptide, or the target polypeptide (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g. antibodies, fusion proteins, peptides, or small molecules) to antagonize the interaction between a given set of polypeptides can be accomplished by determining the activity of one or more members of the set of polypeptides. For example, the activity of PD-1, a PD-1 ligand, a B7 polypeptide, CTLA4, or CD28 can be determined by detecting induction of a cellular second messenger (e.g., tyrosine kinase activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by PD-1, a PD-1 ligand, a B7 polypeptide, CTLA4, or CD28. Determining the ability of the blocking agent to bind to or interact with said polypeptide can be accomplished, for example, by measuring the ability of a compound to modulate immune cell costimulation or inhibition in a proliferation assay, or by interfering with the ability of said polypeptide to bind to antibodies that recognize a portion thereof.

Agents that block or inhibit interaction of a PD-1 ligand with a costimulatory receptor (e.g., soluble forms of PD-1 ligand or blocking antibodies to PD-1 ligand) as well as agents that promote a PD-1 ligand-mediated inhibitory signal (e.g., agents which block the interaction of the PD-1 ligand with a B7 polypeptide) can be identified by their ability to inhibit immune cell proliferation, and/or effector function, or to induce anergy when added to an in vitro assay. For example, cells can be cultured in the presence of an agent that stimulates signal transduction via an activating receptor. A number of recognized readouts of cell activation can be employed to measure, cell proliferation or effector function (e.g., antibody production, cytokine production, phagocytosis) in the presence of the activating agent. The ability of a test agent to block this activation can be readily determined by measuring the ability of the agent to effect a decrease in proliferation or effector function being measured, using techniques known in the art.

For example, agents of this invention can be tested for the ability to inhibit or enhance costimulation in a T cell assay, as described in Freeman et al. (2000) *J. Exp. Med.* 192:1027 and Latchman et al. (2001) *Nat. Immunol.* 2:261. CD4+ T cells can be isolated from human PBMCs and stimulated with activating anti-CD3 antibody. Proliferation of T cells can be measured by $^3$H thymidine incorporation. An assay can be performed with or without CD28 costimulation in the assay. Similar assays can be performed with Jurkat T cells and PHA-blasts from PBMCs.

In yet another embodiment, an assay of the present invention is a cell-free assay in which PD-1, a PD-1 ligand, a B7 polypeptide, CTLA4, or CD28, or a biologically active portion thereof, is contacted with a test compound, and the ability of the test compound to bind to the polypeptide, or biologically active portion thereof, is determined. Binding of the test compound to the PD-1, PD-1 ligand, B7 polypeptide, CTLA4, or CD28 can be determined either directly or indirectly as described above. In a preferred embodiment, the assay includes contacting the polypeptide, or biologically active portion thereof, with its binding partner to form an assay mixture, contacting the assay mixture with a test compound, and determining the ability of the test compound to interact with the polypeptide in the assay mixture, wherein determining the ability of the test compound to interact with the polypeptide comprises determining the ability of the test compound to preferentially bind to the polypeptide or biologically active portion thereof, as compared to the binding partner.

For example, a PD-1 ligand and a B7 polypeptide can be used to form an assay mixture and the ability of a polypeptide to block this interaction can be tested by determining the ability of PD-1 to bind the PD-1 ligand and determining the ability of the PD-1 ligand to bind the B7 polypeptide, by one of the methods described above for determining direct binding. Determining the ability of the PD-1 to bind the PD-1 ligand and determining the ability of the PD-1 ligand to bind the B7 polypeptide can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. PD-1, PD-1 ligand, and B7 polypeptide can be immobilized on a BIAcore chip and multiple agents (blocking antibodies, fusion proteins, peptides, or small molecules) can be tested for binding to PD-1, PD-1 ligand, and B7 polypeptide. An example of using the BIA technology is described by Fitz et al. (1997) *Oncogene* 15:613.

The cell-free assays of the present invention are amenable to use of both soluble and/or membrane-bound forms of proteins (e.g., a PD-1 ligand or PD-1 proteins or biologically active portions thereof, or binding partners to which a PD-1 ligand or PD-1 binds). In the case of cell-free assays in which a membrane-bound form protein is used (e.g., a cell surface PD-1 ligand or PD-1 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either PD-1, a PD-1 ligand, and a B7 polypeptide, or an appropriate target polypeptide, to facilitate separation of complexed from uncomplexed forms of one or both of the proteins, as well as to accommodate automation of the assay. Binding of a test compound to PD-1, a PD-1 ligand, or a B7 polypeptide, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/PD-1, PD-1 ligand, or B7 polypeptide fusion proteins, or glutathione-S-transferase/target fusion proteins, can be adsorbed onto glutathione sepharose beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of PD-1, PD-1 ligand, or B7 polypeptide binding or activity determined using standard techniques.

In an alternative embodiment, determining the ability of the test compound to modulate the activity of PD-1, a PD-1 ligand, or a B7 polypeptide can be accomplished by determining the ability of the test compound to modulate the activity of a polypeptide that functions downstream of PD-1, the PD-1 ligand, or the B7 polypeptide, e.g., a polypeptide that interacts with the PD-1 ligand, or a polypeptide that functions downstream of PD-1, e.g., by interacting with the cytoplasmic domain of PD-1. For example, levels of second messengers can be determined, the activity of the interactor polypeptide on an appropriate target can be determined, or the binding of the interactor to an appropriate target can be determined as previously described.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IV. Pharmaceutical Compositions

PD-1, PD-1 ligand, B7, CTLA4, or CD28 modulating agents (e.g., agents that inhibit or promote the interaction of PD-1 and PD-1 ligand without blocking the interaction of PD-1 ligand and a B7 polypeptide or agents that block the interaction of PD-1 ligand with a B7 polypeptide, including, e.g., blocking antibodies, peptides, fusion proteins, or small molecules) can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., antibodies against PD-1, a PD-1 ligand, a B7 polypeptide, CTLA4, or CD28 fragments of said molecules; or small molecules that block the interactions of said polypeptides) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered it he form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The modulatory agents described herein can be used for methods of treatment (e.g., by up- or down-modulating the immune response). For example, PD-1 ligand binding to PD-1 transmits a negative signal, whereas PD-1 ligand binding to a B7 polypeptide such as B7-1 does not. Thus, modulation of the interaction between PD-1 and a PD-1 ligand, or between a PD-1 ligand and a B7 polypeptide, results in modulation of the immune response. The interaction between a B7 polypeptide and a PD-1 ligand also prevents the PD-1 ligand from binding to PD-1, and thus, inhibits delivering an inhibitory immune signal. Thus, in one embodiment, agents which block the interaction between PD-1 and a PD-1 ligand can prevent inhibitory signaling. In one embodiment, agents that block the binding of a B7 polypeptide to a PD-1 ligand allow the PD-1 ligand to bind PD-1 and provide an inhibitory signal to an immune cell. The PD-1 ligand, by binding to a B7 polypeptide, also reduces B7 binding to the inhibitory receptor CTLA4. In one embodiment, agents that block the binding of a B7 polypeptide to a PD-1 ligand allow the B7 polypeptide to bind CTLA4 and provide an inhibitory signal to an immune cell. In another embodiment, a PD-1 ligand, by binding to a B7 polypeptide, also reduces the B7 polypeptide binding to the costimulatory receptor CD28. Thus, in one embodiment, agents that block the binding of a B7 polypeptide to a PD-1 ligand polypeptide allow the B7 polypeptide to bind CD28 and provide a costimulatory signal to an immune cell.

1. Prophylactic Methods

In one aspect, the invention relates to a method for preventing in a subject, a disease or condition associated with an unwanted or less than desirable immune response. Subjects at risk for a disease that would benefit from treatment with the claimed agents or methods can be identified, for example, by any or a combination of diagnostic or prognostic assays known in the art. Administration of a prophylactic agent can occur prior to the manifestation of symptoms associated with an unwanted or less than desirable immune response. The appropriate agent used for treatment (e.g. antibodies, peptides, fusion proteins or small molecules) can be determined based on clinical indications and can be identified, e.g., using screening assays described herein.

2. Therapeutic Methods

Another aspect of the invention pertains to therapeutic methods of modulating an immune response, e.g., by modulating the interaction between a PD-1 ligand and a B7 polypeptide. For example, modulation of the interaction between PD-1 and a PD-1 ligand, or between a PD-1 ligand and a B7 polypeptide, results in modulation of the immune response.

The interaction between a B7 polypeptide and a PD-1 ligand also prevents the PD-1 ligand from binding to PD-1 and, thus, inhibits delivery of an inhibitory immune signal. Thus, in one embodiment, agents which block the interaction between PD-1 and the PD-1 ligand can prevent inhibitory signaling. In one embodiment, agents that block the binding of a B7 polypeptide to a PD-1 ligand polypeptide allow PD-1 ligand to bind PD-1 and provide an inhibitory signal to an immune cell. PD-1 ligand, by binding to a B7 polypeptide, also reduces the B7 polypeptide binding to the inhibitory receptor CTLA4. In one embodiment, agents that block the binding of a B7 polypeptide to a PD-1 ligand allow the B7 polypeptide to bind CTLA4, and thus provide an inhibitory signal to an immune cell. In another embodiment, a PD-1 ligand, by binding to a B7 polypeptide, also reduces the B7 polypeptide binding to the costimulatory receptor CD28. Thus, in one embodiment, agents that block the binding of a B7 polypeptide to a PD-1 ligand allow the B7 polypeptide to bind CD28, and thus provide a costimulatory signal to an immune cell.

An exemplary agent that modulates the interaction between a PD-1 ligand and PD-1, a B7 polypeptide and CTLA4, a B7 polypeptide and CD28, or a PD-1 ligand and a B7 polypeptide, includes such agents as described herein, e.g. antibodies against PD-1, PD-1 ligand, CTLA4, CD28, or a B7 polypeptide; fragments or peptides derived from PD-1, PD-1 ligand, CD28, CTLA4, or a B7 polypeptide; fusion proteins of PD-1, PD-1 ligand, CD28, CTLA4, or a B7 polypeptide; and small molecules that modulate the interaction of PD-1 with PD-1 ligand, a B7 polypeptide with CD28, a B7 polypeptide with CTLA4, or a PD-1 ligand with a B7 polypeptide.

These modulatory agents can be administered in vitro (e.g., by contacting the cell with the agent) or, alternatively, in vivo (e.g., by administering the agent to a subject). As such, the present invention relates to methods of treating an individual afflicted with a disease or disorder that would benefit from modulation of an immune response, e.g., by modulation of the interaction between a PD-1 ligand and PD-1, or a B7 polypeptide.

3. Downregulation of Immune Responses by Modulation

There are numerous embodiments of the invention for upregulating the inhibitory function or downregulating the costimulatory function of a PD-1 ligand to thereby downregulate immune responses. Downregulation can be in the form of inhibiting or blocking an immune response already in progress, or may involve preventing the induction of an immune response. The functions of activated immune cells can be inhibited by downregulating immune cell responses, or by inducing specific anergy in immune cells, or both.

For example, the immune response can be downmodulated using: PD-1 ligand polypeptides (e.g., soluble, monomeric forms of a PD-1 ligand polypeptide such as PD-1 ligand-Ig) and/or anti-PD-1 ligand antibodies that block the interaction of PD-1 ligand with a B7 polypeptide (e.g., while not affecting or increasing the interaction between PD-L1 and PD-1) or which promote the binding of a PD-1 ligand with PD-1, (e.g., while not affecting or while inhibiting the interaction between a B7 polypeptide and the PD-1 ligand). Other exemplary agents which can block these interactions include anti-B7 polypeptide, a B7 polypeptide, or a blocking small molecule.

Agents that promote binding of a PD-1 ligand to PD-1 or a B7 polypeptide to CTLA4, while not affecting or reducing the binding of the PD-1 ligand to the B7 polypeptide, can also be used to down modulate the immune response. Exemplary agents include PD-1 peptide mimetics, identified by the methods described herein.

In one embodiment of the invention, tolerance is induced against specific antigens by co-administering an antigen with an agent (e.g. antibody, peptide, fusion protein, or small molecule) which blocks the interaction between a PD-1 ligand and a B7 polypeptide. For example, tolerance can be induced to specific proteins. In one embodiment, immune responses to allergens, or to foreign proteins to which an immune response is undesirable, can be inhibited. For example, patients that receive Factor VIII frequently generate antibodies against this clotting factor. Co-administration of an agent that blocks a PD-1 ligand-mediated costimulatory signal or an agent that stimulates a PD-1 mediated inhibitory signal in combination with recombinant factor VIII (or by physically linked to Factor VIII, e.g., by cross-linking) can result in downmodulation.

In one embodiment, fusion proteins comprising a first PD-1 ligand peptide fused to a second peptide can be used to block the interaction of the PD-1 ligand with a B7 polypeptide on an immune cell, to thereby downmodulate immune responses. In one embodiment, the second peptide blocks an activity of another B lymphocyte antigen (e.g., B7-1, B7-2, or B7-3) to further downmodulate immune responses. Alternatively, two separate agents that downmodulate immune responses can be combined as a single composition or administered separately (simultaneously or sequentially) to more effectively downregulate immune cell mediated immune responses in a subject. For instance, a PD-1 ligand can be combined with a B7 polypeptide, or with a combination of blocking antibodies (e.g., antibodies against a PD-1 ligand polypeptide with anti-B7-1 and/or anti-B7-2 monoclonal antibodies). Furthermore, a therapeutically active amount of one or more of the subject agents, can be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), and immunosuppressive drugs, (e.g., rapamycin, cyclosporine A or FK506).

Downregulating or preventing a PD-1 ligand interaction with a B7 polypeptide, or promoting an interaction between a PD-1 ligand and PD-1 (for example, without modulating, or by additionally enhancing) the interaction between the PD-1 ligand and the B7 polypeptide (e.g. by stimulation of the negative signaling function of PD-1) is useful to downmodulate the immune response, e.g., in situations of tissue, skin and organ transplantation, in graft-versus-host disease (GVHD), or in autoimmune diseases such as systemic lupus erythematosus, and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a polypeptide which inhibits or blocks interaction of a PD-1 ligand with a B7 polypeptide (such as a soluble, monomeric form of the PD-1 ligand or PD-1), alone or in conjunction with another downmodulatory agent, prior to or at the time of transplantation can promote the generation of an inhibitory signal. Moreover, inhibition of PD-1 ligand costimulatory signals, or promotion of a PD-1 ligand or PD-1 inhibitory signals, may also be sufficient to anergize the immune cells, thereby inducing tolerance in a subject. Induction of long-term tolerance by blocking a PD-1 ligand mediated costimulatory signal may avoid the necessity of repeated administration of these blocking reagents.

To achieve sufficient immunosuppression or tolerance in a subject, it may also be desirable to block the costimulatory function of other polypeptides. For example, it may be desirable to block the function of B7-1, B7-2, or B7-1 and B7-2 by administering a soluble form of a combination of peptides having an activity of each of these antigens, blocking antibodies against these antigens or blocking small molecules (separately or together in a single composition) prior to or at the time of transplantation. Alternatively, it may be desirable to promote inhibitory activity of a PD-1 ligand or PD-1 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs.

Downmodulation of immune responses are also useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of reagents which block costimulation of immune cells by disrupting interactions between PD-1 ligand and B7 polypeptides, or by promoting the interaction between PD-1 ligand and PD-1, without modulating or while downmodulating the interaction between PD-1 ligand and a B7 polypeptide, are useful for inhibiting immune cell activation and preventing production of autoantibodies or cytokines which may be involved in the disease process. Additionally, agents that promote an inhibitory function of a PD-1 ligand or PD-1 may induce antigen-specific tolerance of autoreactive immune cells, which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., *Fundamental Immunology*, Raven Press, New York, Third Edition 1993, chapter 30).

Inhibition of immune cell activation is useful therapeutically in the treatment of allergy and allergic reactions, e.g., by inhibiting IgE production. An agent that promotes a PD-1 ligand or PD-1 inhibitory function can be administered to an allergic subject to inhibit immune cell mediated allergic responses in the subject. Inhibition of PD-1 ligand costimulation of immune cells or stimulation of a PD-1 ligand or PD-1 inhibitory pathway can be accompanied by exposure to allergen in conjunction with appropriate MHC polypeptides. Allergic reactions can be systemic or local in nature, depending on the route of entry of the allergen and the pattern of deposition of IgE on mast cells or basophils. Thus, inhibition of immune cell mediated allergic responses locally or systemically by administration of an inhibitory form of an agent that inhibits the interaction of a PD-1 ligand with a costimulatory receptor, or an agent that promotes an inhibitory function of a PD-1 ligand or PD-1.

Inhibition of immune cell activation through blockage of the interaction of a PD-1 ligand and a B7 polypeptide, or through promotion of the interaction between a PD-1 ligand and PD-1, without modulating or while downmodulating the interaction between the PD-1 ligand and a B7 polypeptide, may also be important therapeutically in viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. PD-1 ligand is normally highly expressed in placental trophoblasts, the layer of cells that forms the interface between mother and fetus and may play a role in preventing maternal rejection of the fetus. Females at risk for spontaneous abortion (e.g., those who have previously had a spontaneous abortion or those who have had difficulty conceiving) because of immunologic rejection of the embryo or fetus can be treated with agents that modulate these interactions.

Downregulation of an immune response by modulation of PD-1 ligand/B7 polypeptide, binding or by modulation of PD-1 ligand/PD-1 binding may also be useful in treating an autoimmune attack of autologous tissues. For example, PD-1 ligand is normally highly expressed in the heart and may protect the heart from autoimmune attack. This is evidenced by the fact that the Balb/c PD-1 knockout mouse exhibits massive autoimmune attack on the heart with thrombosis. Thus, conditions that are caused or exacerbated by autoimmune attack (e.g., in this example, heart disease, myocardial infarction or atherosclerosis) may be ameliorated or improved by modulation of these interactions. It is therefore within the scope of the invention to modulate conditions exacerbated by autoimmune attack, such as autoimmune disorders (as well as conditions such as heart disease, myocardial infarction, and atherosclerosi).

4. Upregulation of Immune Responses

Also useful therapeutically is the blockage of the interaction of a PD-1 ligand with PD-1, and/or a B7 polypeptide with CTLA4, without modulating or while upregulating the interaction between the B7 polypeptide and the PD-1 ligand, or by promoting the interaction of the PD-1 ligand with the B7 polypeptide (e.g., while not affecting or while inhibiting the interaction between the PD-1 ligand and PD-1) as a means of upregulating an immune response. Blocking the interaction between a B7 polypeptide and a PD-1 ligand to thereby increase the interaction between the B7 polypeptide and CD28, is also useful to upregulate immune responses. Upregulation of immune responses can be in the form of enhancing an existing immune response or eliciting an initial immune response. For instance, enhancing an immune response using the subject compositions and methods is useful in cases of infections with microbes (e.g., bacteria, viruses, or parasites). In one embodiment, an agent that blocks the interaction of a PD-1 ligand with PD-1, without modulating or while upregulating the interaction between a B7 polypeptide and the PD-1 ligand, or by promoting the interaction of the PD-1 ligand with the B7 polypeptide, is used to enhance the immune response. Such an agent (e.g., a non-activating antibody that blocks PD-L1 binding to PD-1) is therapeutically useful in situations where upregulation of antibody and cell-mediated responses would be beneficial. In a preferred embodiment, the agent inhibits the interaction between PD-1 and a PD-1 ligand, without inhibiting the interaction between the PD-1 ligand and a B7 polypeptide (e.g., an interaction which prevents PD-L1 from binding to PD-1). Exemplary disorders include viral skin diseases, such as Herpes or shingles, in which case such an agent can be delivered topically to the skin. In addition, systemic viral diseases such as influenza, the common cold, and encephalitis might be alleviated by systemic administration of such agents.

Alternatively, immune responses can be enhanced in an infected patient through an ex vivo approach, for instance, by removing immune cells from the patient, contacting immune cells in vitro with an agent that blocks the interaction of a PD-1 ligand with PD-1, without modulating or while upmodulating the interaction between a B7 polypeptide and the PD-1 ligand, or by promoting the interaction of the PD-1 ligand with the B7 polypeptide, and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response.

An agent that blocks the interaction of a PD-1 ligand with PD-1 (e.g., without modulating or while upmodulating the interaction between a B7 polypeptide and the PD-1 ligand or by enhancing the interaction of the PD-1 ligand with the B7 polypeptide) can be used prophylactically in vaccines against various polypeptides (e.g., polypeptides derived from pathogens). Immunity against a pathogen (e.g., a virus) can be induced by vaccinating with a viral protein along with an agent that blocks the interaction of a PD-1 ligand with PD-1, without modulating or while upmodulating the interaction between a B7 polypeptide and the PD-1 ligand, or by promoting the interaction of the PD-1 ligand with the B7 polypeptide, in an appropriate adjuvant.

In another embodiment, upregulation or enhancement of an immune response function, as described herein, is useful in the induction of tumor immunity In another embodiment, the immune response can be stimulated by the methods described herein, such that preexisting tolerance is overcome. For example, immune responses against antigens to which a subject cannot mount a significant immune response, e.g., to an autologous antigen, such as a tumor specific antigens can be induced by administering an agent that blocks the interaction of a PD-1 ligand with PD-1 (e.g., without modulating or while upmodulating the interaction between a B7 polypeptide and the PD-1 ligand or by promoting the interaction of the PD-1 ligand with the B7 polypeptide). In one embodiment, a soluble PD-1 or a soluble PD-1 ligand that inhibits the interaction of a PD-1 ligand with PD-1, without modulating or while upmodulating the interaction between a B7 polypeptide and the PD-1 ligand, or by promoting the interaction of the PD-1 ligand with the B7 polypeptide, can be used to enhance an immune response (e.g., to a tumor cell). In one embodiment, an autologous antigen, such as a tumor-specific antigen can be coadministered. In another embodiment, an immune response can be stimulated against an antigen (e.g., an autologous antigen) to treat a neurological disorder. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

V. Administration of Agents

The immune modulating agents of the invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an anti-PD-1 ligand modulating agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) J. Neuroimmunol. 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

This invention is further illustrated by the following examples which should not be construed as limiting. The contents of all references, patents and published patent applications cited throughout this application, as well as the Figures, are incorporated herein by reference.

EXAMPLES

Example 1

Identification of PD-1 L1Ligand and B7 as Binding Partners

In order to identify new B7-1 binding partners other than CD28 and CTLA4, a cDNA library from CD28/CTLA4 deficient mice was screened. A murine cDNA library in the pAXEF mammalian expression vector was made from RNA prepared from CD4+ T cells of CD28 deficient, CTLA4 deficient 129 strain mice. CD4+ T cells were purified by MACS, with purity greater than 95% confirmed by flow cytometry. The T cells were activated with anti-CD3 mAb plus antigen presenting cells (APC). APCs from T-depleted splenocytes of CD28 deficient, CTLA4 deficient 129 strain mice were stimulated overnight with 5 μg/ml of the anti-CD40 mAb 3/23, then treated with mitomycin C (50 μg/ml for 40 minutes at 37° C.), washed, and used to stimulate T cells. RNA was prepared after 16, 24, and 40 hr and combined for preparation of the cDNA library.

For the first round of selection, 80 plates of COS cells were transfected via the DEAE-Dextran procedure with 0.2 μg of plasmid library DNA per 100 mm dish. Cells were trypsinized and replated the next day and after 45 hr, cells were harvested with 0.5 mM EDTA, 0.02% sodium azide in PBS. Panning plates were prepared by incubating a 100 mm petri dish with 10 ml of 10 μg/ml goat anti-mouse IgG2a antibody in 50 mM Tris, pH 9.5 for 1.5 hours at room temperature. The plate was washed 3 times with PBS and blocked overnight in PBS plus 5 mg/ml BSA. The plate was then incubated 1 hr with 3 ml of 10 μg/ml murine B7-1-IgG2a fusion protein, washed three times with PBS, 2% FCS. Transfected COS cells from 80 plates were incubated on 8 panning plates. After 2 hours at room temperature, the plates were washed 3 times with 0.5 mM EDTA, 0.02% sodium azide, 2% FCS in PBS and then twice with 0.5 mM EDTA, 10 mM HEPES, pH 7.4, 1% FCS in 0.15 M NaCl. Episomal DNA was prepared from adherent cells, re-introduced into *E. Coli* DH10B/P3 by electroporation, transfected into COS cells by polyethylene glycol-mediated fusion of spheroplasts and the panning repeated. Episomal DNA was prepared from adherent cells, re-introduced into *E. Coli* DH10B/P3 by electroporation, transfected into COS cells by polyethylene glycol-mediated fusion of spheroplasts and the panning was repeated a third time. Individual plasmid DNAs were prepared and sequenced. All of the plasmids (of 6 sequenced) were found to contain a cDNA encoding murine PD-L1. The cDNA clones varied slightly in the length of the 5' untranslated region, indicating that the PD-L1 gene was independently isolated multiple times, thus excluding the possibility of accidental isolation of a clone previously generated in the lab. These murine PD-L1 cDNA clones were transfected into COS cells via the DEAE-Dextran procedure (4 μg per 100 mm dish) and analyzed after 72 hr for cell surface binding of murine B7-1-IgG2a fusion protein by indirect immunofluorescence and flow cytometry.

Example 2

Binding of PD-1 Ligand Molecules to B7 Molecules

Mouse pre-B cells (300.19) were transfected with either vector DNA (pcDNAI), or an expression plasmid containing the murine PD-L1 cDNA in the pAXEF vector, together with a plasmid encoding puromycin resistance. Cells were selected in media containing 10 μg/ml puromycin, stained with PD-1-IgG2a fusion protein, sorted, and subcloned. A clone expressing high levels of PD-L1 was selected for further analysis.

300.19 transfectants ($5 \times 10^6$ cells in 2.5 ml media) were labeled with 2.5 μl of BCECF-AM (Molecular Probes, 5 mg/ml in DMSO, 2',7'-(bis-2-carboxyethyl)-5-(and-6)-carboxyfluorescein)) for 15 minutes at 37°. Cells were washed twice and 50,000 cells in 50 μl used per well.

Figure 2:
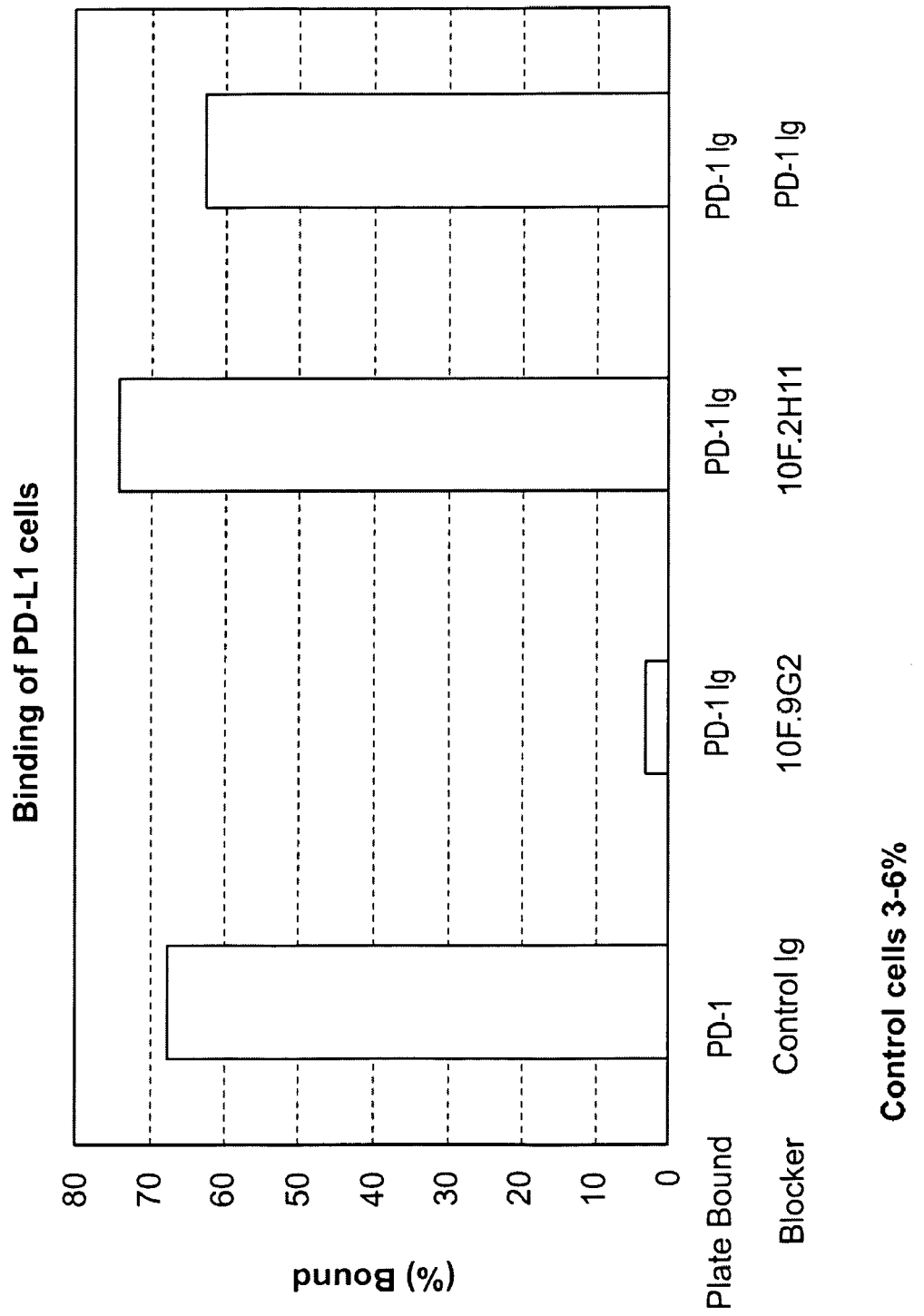
FIG. 2 is a bar graph of data representing the binding of cells expressing PD-L1 to PD-1 Ig, in the presence and absence of the 10F.9G2 antibody. The data indicates that the 10F.9G2 antibody inhibits this interaction.
Figure 3:
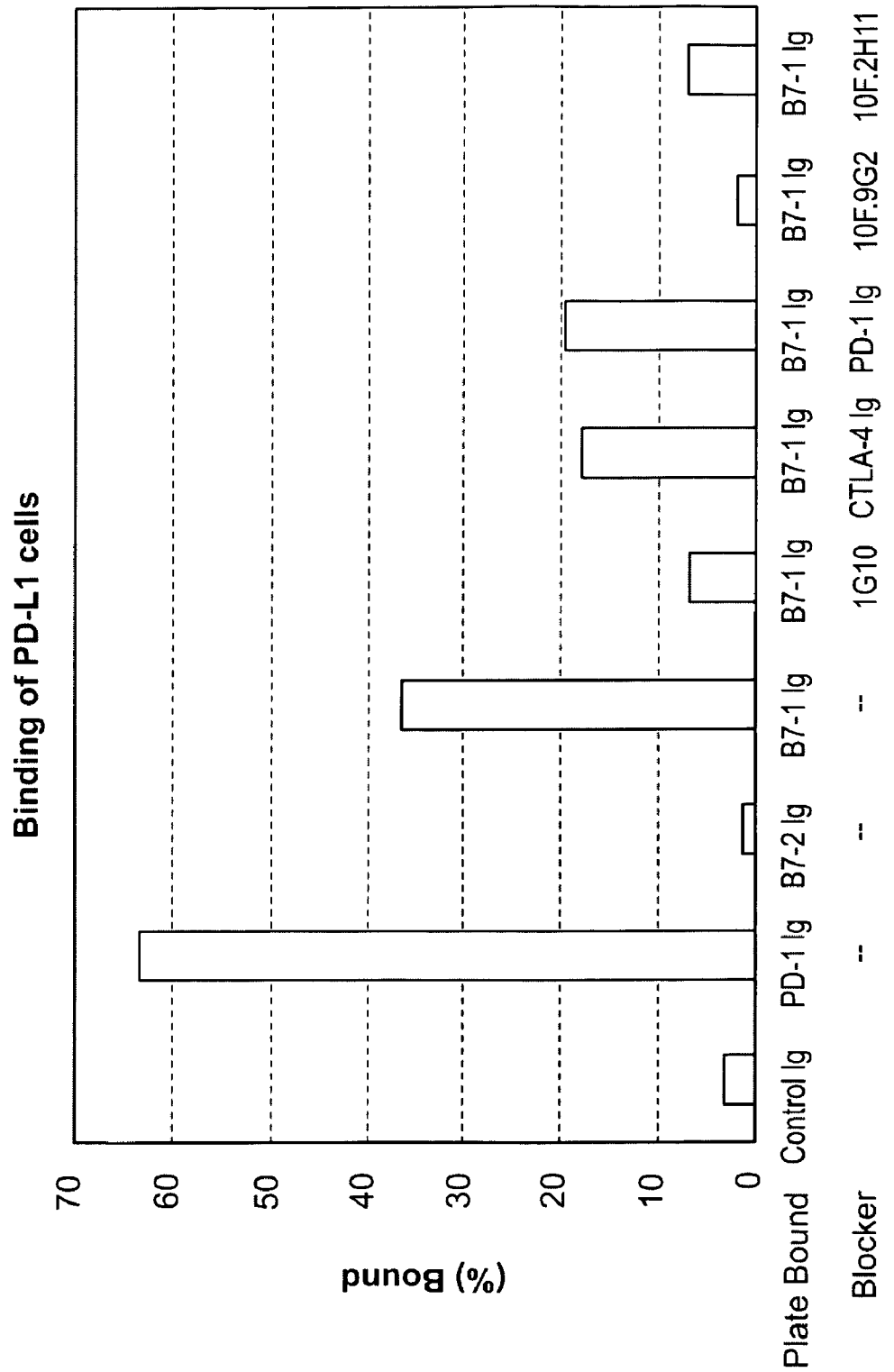
FIG. 3 is a bar graph of data representing the binding of cells expressing PD-L1 to B7-1 and B7-2. illustrates the compares the ability of B7-1 and B7-2 to bind to cells expressing PD-L1.

LINBRO™ 96 well microtiter plates (not tissue culture treated) were coated with 100 μl of 10 μg/ml goat anti-mouse IgG2a antibody in PBS overnight at 4°. Plates were aspirated and blocked for 2 hr with 1% BSA in PBS. Wells were then incubated with 0.1 ml of 10 μg/ml control Ig, B7-1 Ig, B7-2 Ig, or PD-1 Ig. 50,000 BCECF-AM-labeled transfected cells were added to the plates in the presence or absence of a blocker. The blockers tested were 10 μg/ml control Ig, CTLA4 Ig, PD-1 Ig, the 1G10 antibody (which binds to murine B7-1 and blocks its interaction with CTLA4), the 16-10A1 antibody (which binds to murine B7-1 and blocks its interaction with CTLA4), the 10F.9G2 antibody (which binds to murine PD-L1 and blocks its interaction with PD-1), and the 10F.2H11 antibody (which binds to murine PD-L1 but does not block its interaction with PD-1). The plates were centrifuged 10 sec at 700 rpm and incubated at room temperature for 30 minutes. The fluorescence in each well (indicating the number of cells) was measured on a fluorescence plate reader. The plates were washed 1× by submerging the plate in a large volume of 1% BSA/PBS in a dish, gently inverting the plate, and allowing non-adherent cells to fall at 1 g for 30 min at room temperature. The wash was then repeated. The plate was then righted and the fluorescence in each well (indicating the number of cells) was measured on a fluorescence plate reader. The percent of cells bound to the plate was determined. The PD-L1 expressing cells bound to the B7-1 Ig plates, but not to the B7-2 Ig plates. Neither control Ig or CTLA4 Ig competed in this binding interaction (FIG. 1). In contrast, the 1G10, 10F.9G2, and 10F.2H11 antibodies and PD-1 Ig each competed for binding with the PD-L1/B7-1 Ig interaction and lead to a decrease in cell binding (FIG. 1). In a control experiment, PD-L1 expressing cells were shown to bind to plates coated with PD-1 Ig (FIG. 2). Control Ig, PD-1 Ig, and the 10F.2H11 antibody all failed to compete for binding in this assay (FIG. 2). Only the 10F.9G2 antibody competed for the PD-L1/PD-1 interaction and decreased cell binding (FIG. 2).

Example 3

FACS Analysis of PD-1 Ligand Molecules 300.19 cells were transfected with either vector DNA (pcDNAI), or an expression plasmid containing the ICOS ligand, mPD-L1 or mPD-L2 cDNA.

Figure 4A:
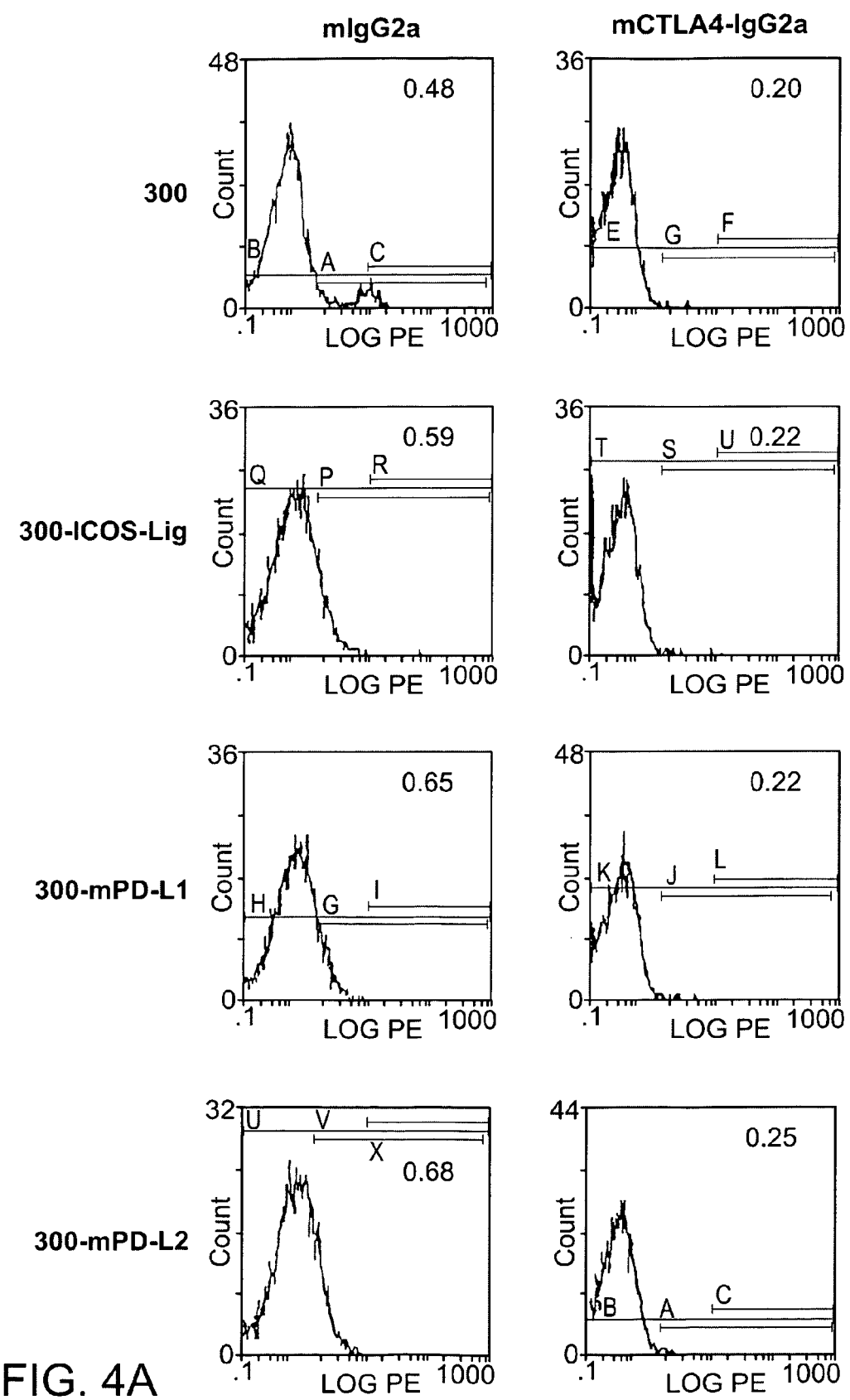
FIG. 4 is a graphical representation of data generated by FACS analysis, which indicates murine PD-1 binding to murine PD-L1 and PD-L2.
Figure 4B:
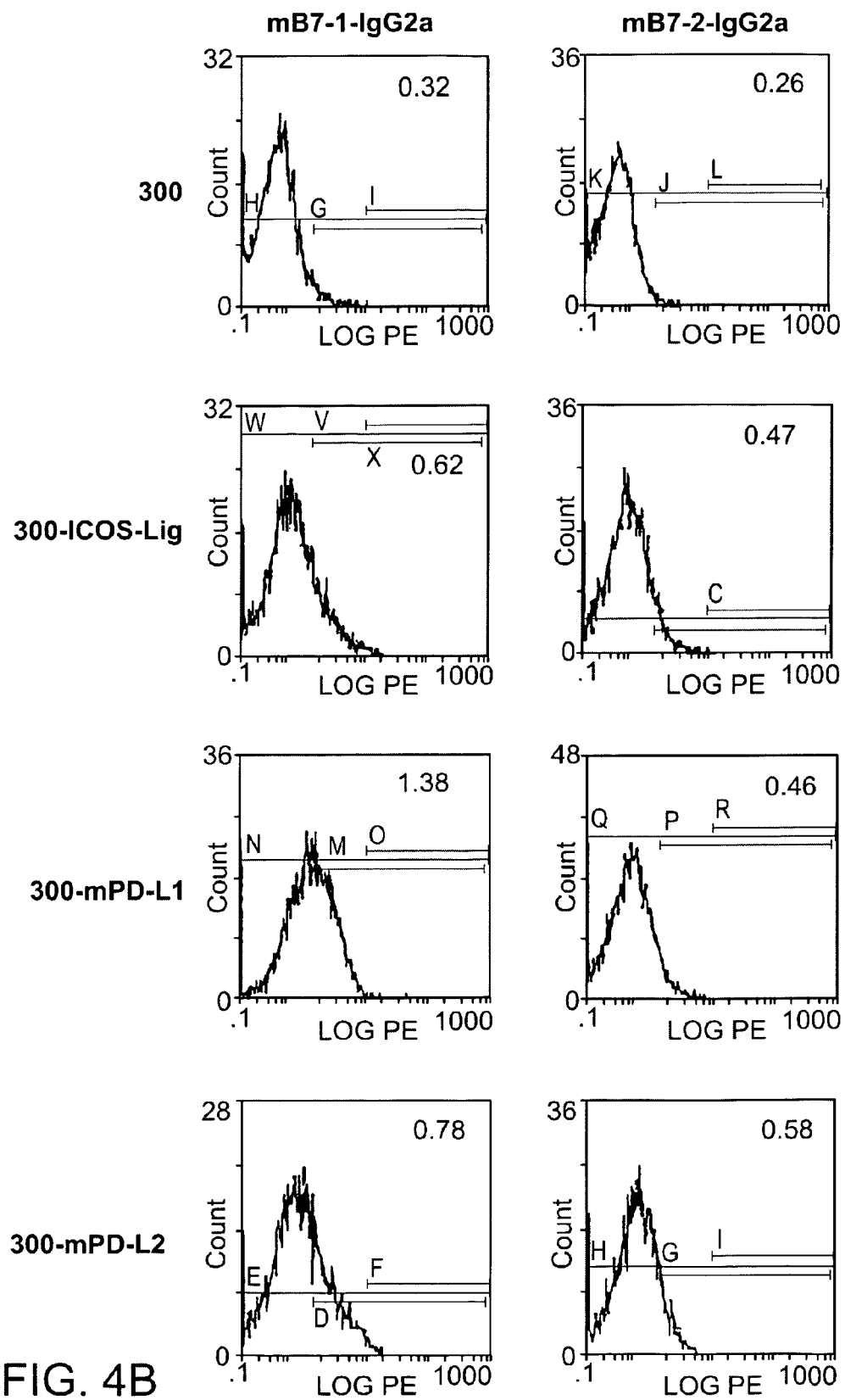
Figure 4C:
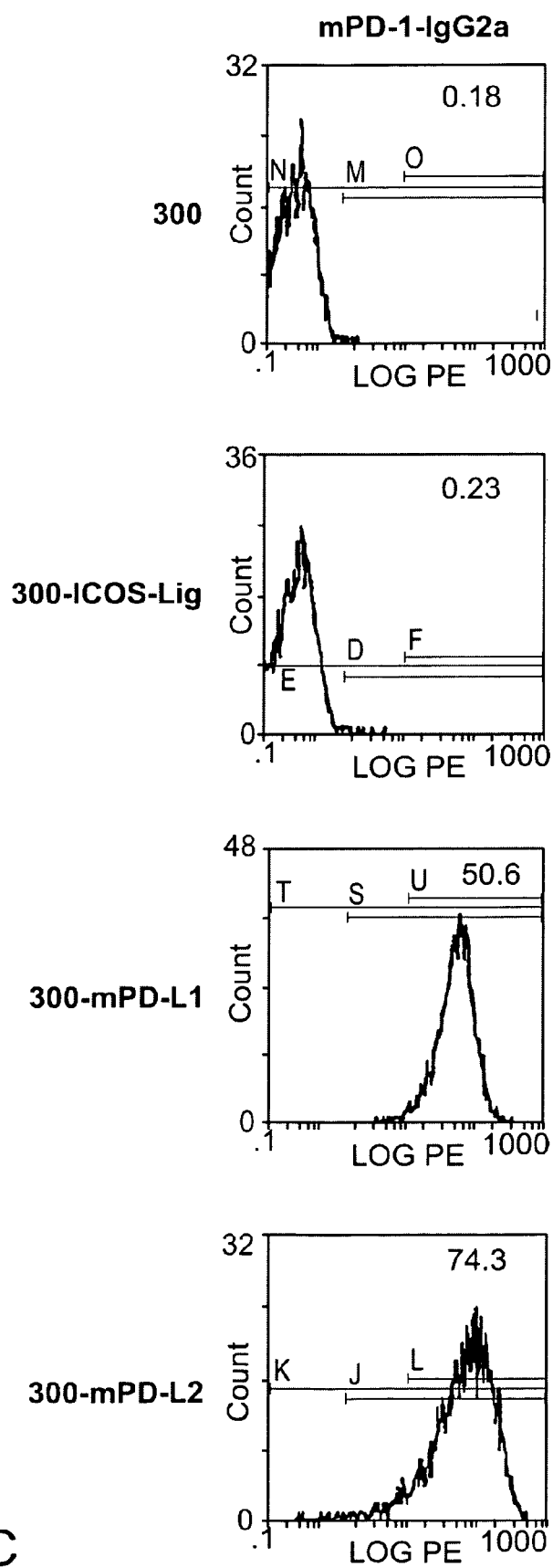

Cells were incubated with mIgG2a, mCTLA4-IgG2a, mB7-1-IgG2a, mB7-2-IgG2a, or mPD-1-IgG2a (0.1 ml of 10 μg/ml) for 30 minutes at 4° C. Cells were washed with FACS buffer (PBS plus 0.02% sodium azide and 2% FBS) and incubated with PE labeled goat anti-mIgG2a antibody (0.1 ml of 10 μg/ml) (Southern Biotech Associates). Cells were analyzed for immunoflourescence using FACS analysis and the results are shown in FIG. 4 (the numbers in FIG. 4 indicate the mean fluorescence intensity). There was no binding to the ICOS ligand or control cells. The PD-L1 cells bound to mPD-1-IgG2a and mB7-1-IgG2a, but not to mCTLA4-IgG2a or mB7-2-IgG2a. The PD-L2 cells bound to mPD-1-IgG2a and mB7-1-IgG2a (slightly), but not to mCTLA4-IgG2a or mB7-2-IgG2a (FIG. 4).

The invention claimed is:

1. A method for inhibiting the interaction between a B7-1 polypeptide and a PD-L1 polypeptide, comprising:
   a) contacting an immune cell bearing a PD-L1 polypeptide; or
   b) contacting an immune cell bearing a B7-1 polypeptide; with an agent that inhibits the interaction between the PD-L1 polypeptide and the B7-1 polypeptide.

2. The method of claim 1, wherein the agent is an anti-PD-L1 antibody.

3. The method of claim 1, wherein said inhibition of the interaction between the PD-L1 polypeptide and the B7-1 polypeptide provides an inhibitory signal to the immune cell.

4. The method of claim 1, wherein the inhibition of interaction between the PD-L1 polypeptide and the B7-1 polypeptide allows the binding of the B7-1 polypeptide to CTLA-4.

5. The method of claim 1, wherein the inhibition of interaction between the PD-L1 polypeptide and the B7-1 polypeptide allows the binding of the B7-1 polypeptide to CD28.

6. The method of claim 1, wherein said immune cell is a monocyte.

7. The method of claim 1, wherein said immune cell is a dendritic cell.

* * * * *

UNITED STATES PATENT AND TRADEMARK OFFICE
CERTIFICATE OF CORRECTION

| | | |
|---|---|---|
| PATENT NO. | : 7,722,868 B2 | Page 1 of 1 |
| APPLICATION NO. | : 11/501392 | |
| DATED | : May 25, 2010 | |
| INVENTOR(S) | : Gordon J. Freeman et al. | |

It is certified that error appears in the above-identified patent and that said Letters Patent is hereby corrected as shown below:

In the Specification

At column 1, lines 15-18 under Government Funding should read:

--This invention was made with government support under AI039671, CA084500 and AI041584, awarded by the National Institutes of Health. The government has certain rights in the invention.--

Signed and Sealed this
Twenty-fifth Day of August, 2015

Michelle K. Lee
*Director of the United States Patent and Trademark Office*